US008512258B2

(12) United States Patent
Ben Oren et al.

(10) Patent No.: US 8,512,258 B2
(45) Date of Patent: *Aug. 20, 2013

(54) BREATH TEST DEVICE AND METHOD

(75) Inventors: Ilan Ben Oren, Modiin (IL); Gil Guggenheim, Jerusalem (IL); Avraham Hershkowitz, Shimshon (IL); Dario Vertnik, Raphael Klachkin (IL); Mori Arkin, Kfar Shmaryahu (IL); Mira Kremer, Kochav Yair (IL); Yaron Ilan, Jerusalem (IL)

(73) Assignee: Exalenz Bioscience Ltd., Modlin (IL)

( * ) Notice: Subject to any disclaimer, the term of this patent is extended or adjusted under 35 U.S.C. 154(b) by 1079 days.

This patent is subject to a terminal disclaimer.

(21) Appl. No.: 12/219,824

(22) Filed: Jul. 29, 2008

(65) Prior Publication Data
US 2009/0131810 A1 May 21, 2009

Related U.S. Application Data

(63) Continuation-in-part of application No. 12/084,629, filed as application No. PCT/IL2006/001296 on Nov. 12, 2006.

(60) Provisional application No. 60/735,479, filed on Nov. 11, 2005.

(51) Int. Cl.
*A61B 5/08* (2006.01)
*A61B 5/083* (2006.01)

(52) U.S. Cl.
USPC .............................. 600/531; 600/532; 600/538

(58) Field of Classification Search
None
See application file for complete search history.

(56) References Cited

U.S. PATENT DOCUMENTS

| 5,386,832 | A | 2/1995 | Wagner |
| 5,486,699 | A | 1/1996 | Fabinski |
| 6,071,245 | A | 6/2000 | Kohno |
| 6,186,958 | B1 | 2/2001 | Katzman et al. |
| 6,491,643 | B2 | 12/2002 | Katzman et al. |
| 6,656,127 | B1 | 12/2003 | Ben-Oren et al. |
| RE38,728 | E | 4/2005 | Katzman et al. |
| 2001/0021815 | A1 | 9/2001 | Katzman et al. |
| 2003/0053049 | A1 | 3/2003 | Fink |
| 2003/0216660 | A1 | 11/2003 | Ben-Oren et al. |

(Continued)

FOREIGN PATENT DOCUMENTS

| WO | 99/12471 | 3/1999 |
| WO | 01/13091 | 2/2001 |
| WO | 2007/054940 | 5/2007 |

OTHER PUBLICATIONS

U.S. Appl. No. 12/084,629, filed May 7, 2008, Ben-Oren, et al.

(Continued)

*Primary Examiner* — Louise Humphrey
(74) *Attorney, Agent, or Firm* — Rodney J. Fuller; Booth Udall Fuller, PLC

(57) ABSTRACT

There is provided a method of evaluating a liver condition of a subject, the method includes computing a fluctuation parameter from a liver breath test based on at least one of a percentage dose recovery (PDR) curve and a delta over baseline (DOB) curve of an isotope labeled methacetin, or a salt or a derivative thereof, and evaluating at least one liver condition of the subject, based at least on the fluctuation parameter. There is provided herein a method of evaluating a liver condition of a subject, the method includes computing a hepatic impairment score based at least on a breath test related parameter and on a demographic parameter.

28 Claims, 5 Drawing Sheets

(56) References Cited

U.S. PATENT DOCUMENTS

| | | |
|---|---|---|
| 2004/0122790 A1 | 6/2004 | Walker |
| 2004/0152994 A1 | 8/2004 | Meier-Augenstein |
| 2004/0253637 A1 | 12/2004 | Buechler |
| 2005/0020931 A1 | 1/2005 | Ben-Oren et al. |
| 2005/0177056 A1 | 8/2005 | Giron |
| 2007/0026480 A1 | 2/2007 | Modak |
| 2007/0135725 A1 | 6/2007 | Hatlestad |
| 2008/0167533 A1 | 7/2008 | Leyendecker |
| 2010/0055734 A1 | 3/2010 | Everson |
| 2010/0143880 A1 | 6/2010 | Stockmann |
| 2010/0329979 A1 | 12/2010 | Modak |

OTHER PUBLICATIONS

Braden, et al, "13 C-methacetin breath test as liver function test in patients with chronic hepatitis C virus infection", Aliment Pharmacol Ther, 2005; 21, pp. 179-185.

Klatt, et al, "Evaluation of the 13 C-methacetin breth test for quantitative liver function testing", Z Gastroenterol. 1997; 35, pp. 609-614.

Kleiner, et al, "Design and Validation of a Histological Scoring System for Nonalcoholic Fatty Liver Disease", Nonalcoholic Steatohepatitis Clinical Research Network, Hepatology, 41(6) Jun. 2005, pp. 1313-1321.

Everson, et al, "The spectrum of hepatic functional impairment in compensated chronic hepatitis C: results from the Hepatitis C Antiviral Long-term Treatment against Cirrhosis Trial", Aliment Pharmacol Ther., May 2008, vol. 27, Issue 9, pp. 798-809.

Kumar, M, et al, Histological subclassification of cirrhosis based on histological-haemodynamic correlation, Aliment Pharmacol Ther., May 2008, 27(9), pp. 771-779 (abstract).

Candelli, et al, "13C-Methacetin Breath Test: A New Tool to Predict the Presence of Liver Vascular Malformations in Patients with Herediatry Haemorragic Teleangiecstasia", AASLD Abstracts, 2007, p. 884A.

Foufelle, Fabienne and Ferre, Pascal, "New perspectives in the regulation of hepatic glycolytic and lipogenic genes by insulin and glucose: a role for the transcription factor sterol regulatory element binding protein-1c", Biochem J, 366(pt 2):377-391 (2002).

Iwasaki, Ayami et al., "Study of liver function in babies with atopic dermatitis by using13C methacetin breath test", Allergy, Japan Office of Japanese Society of Allerology 41(6):645-653 (English abstract) (1992).

Masseroli, Marco et al., "Automatic quantification of liver fibrosis: design and validation of a new image analysis method: comparison with semi-quantitative indexes of fibrosis", J Hepatol, 32(3):453-464 (2000).

Petrolati, A et al., "13C-methacetin breath test for monitoring hepatic function in cirrhotic patients before and after liver transplantation", Aliment Pharmacol Ther, 18:785-790 (2003).

Tingstad, J. et al., "Dissolution rate studies. 3. Effect of type and intensity of agitation on dissolution rate", J Pharm Sci, 62(2):293-297 (1973).

Randle, P. J. et al., "The glucose fatty acid cycle: its role in insulin sensitivity and the metabolic disturbances in diabetes mellitus", Lancet, 281(7285):785-789 (1963).

Harwood Lescher, F., "Recent Materia Medica: Notes on their origin and therapeutics", J. & A. Churchill. Fourth Edition, pp. 70-71 (1891).

N-(-4Methoxyphenyl)acetamide. Chemical Book. Retrieved from http://www.chemicalbook.com/ChemicalProductProperty_EN_CB6310310.htm on Apr. 19, 2012.

ISR of PCT/IL2006/001296 mailed May 11, 2009.

ISR of PCT/IL09/00730 mailed Jan. 11, 2010.

EP 06809856 Supplementary European Search Report Mar. 15, 2011.

How Is Metabolic Syndrome Diagnosed? US Department of Health & Human Services. National Institute of Health. National Heart Lung and Blood Institute. Diseases and Conditions Index. Retrieved from http://nhlbi.nih.gov/health/doi/Diseases/ms diagnosis.html on Sep. 11, 2008.

Histological Scoring System for Nonalcoholic Fatty Liver Disease (NAFLD). Components of NAFLD Activity Score (NAS) and Fibrosis Staging. retrieved from http://www.medicalcriteria.com/criteria/gas nafld.htm on May 31, 2006.

Purified Water (PW) Edstrom Industries, Inc. retrieved from http://www.edstrom.com/Resources.cfm?doc id+174 on Sep. 11, 2008.

Citric Acid Cycle.Wikipedia.org retrieved from http://en.wikipedia.org/wiki/Citric_acid_cycle on Sep. 11, 2008.

Acetyl-CoA. Wikipedia.org retrieved from http://en.wikipedia.org/wiki/Acetyl-CoA on Sep. 11, 2008.

Multivariate analysis. Wikipedia.org retrieved from http://en.wikipedia.org/wiki/ Multivariate analysis on Sep. 11, 2008.

Logistic regression. Wikipedia.org retrieved from http://en.wikipedia.org/wiki/Logistic regression on Sep. 11, 2008.

U.S. Appl. No. 12/084,629 Non-Final Rejection Sep. 6, 2011.

U.S. Appl. No. 12/084,629 Final Rejection Apr. 26, 2012.

BREATH TEST DEVICE AND METHOD

RELATED APPLICATIONS

The present application is a Continuation In Part of U.S. application Ser. No. 12/084,629 (pending), which was filed in the U.S. Patent and Trademark Office on May 7, 2008, which is the National Phase of PCT application PCT/IL2006/001296 filed Nov. 12, 2006, which claims the benefit under 35 U.S.C. 119(e) of US Provisional Application 60/735,479, filed Nov. 11, 2005, the entire disclosure of which is incorporated herein by reference.

BACKGROUND

The foregoing examples of the related art and limitations related therewith are intended to be illustrative and not exclusive. Other limitations of the related art will become apparent to those of skill in the art upon a reading of the specification and a study of the figures.

Liver disease has become one of the most common chronic illnesses, affecting tens of millions of people in the developed world, resulting in lifetime suffering and huge costs to the medical system. Viral hepatitis C(HCV) is one of the leading known causes of liver disease in the United States. It is a common cause of cirrhosis and hepatocellular carcinoma (HCC), as well as the most common reason for liver transplantation. At least 4 million people in the United States are believed to have been infected with HCV, making HCV the most common chronic blood-borne infection nationally. Treatment of HCV has been successful in up to 60% of the cases, depending upon factors such as genotype, ethnicity, co-infections and other risk factors. In addition to the well-known chronic liver diseases due to viral hepatitis C (HCV), there is an increasing population with chronic liver diseases due to alcohol, autoimmune diseases, obesity and diabetes type 2 (associated with metabolic syndrome). Nonalcoholic fatty liver disease (NAFLD) has become a common chronic liver condition due to obesity and diabetes mellitus, affecting almost a quarter of the general population in the United States. The trend of a rise in obesity in the western world is increasing annually. NAFLD includes a spectrum of liver conditions, ranging from simple steatosis (fat accumulation), also referred to as nonalcoholic fatty liver (NAFL), to non-alcoholic steatohepatitis (NASH) disease, which is associated with liver injury. NASH may progress from fibrosis to cirrhosis, as a consequence of the distortion of the normal liver architecture that interferes with blood flow through the liver. Cirrhosis can also lead to an inability of the liver to perform its biochemical functions, resulting in complications that cause liver failure and liver cancer. Then, transplantation would be the only feasible solution, and in many cases, even transplantation is not an option. Currently, there are several treatments in the pipeline for NASH, but there is no known approved and effective treatment currently available.

Breath tests that are based on monitoring the $^{13}CO_2$, which is a by-product of metabolization by the liver of $^{13}C$ labeled substrates, have been proposed as a tool for evaluation of liver function. Previously available tests for liver diseases generally involve drastically invasive procedures, and are therefore much less patient compliant than simple breath tests. Such procedures include biopsies of organs suspected of malfunction, blood tests and imaging technologies. It may take many years, if at all, until liver biopsy will be fully replaced. Although a biopsy is considered to yield reliable results, it is not the optimal tool for patient management since it is highly invasive, expensive, requires day or overnight hospitalization of the patient and is very sensitive to sampling and analysis errors.

Blood tests for the detection of antibodies to suspected bacteria/virus and blood biochemistry tests include standard serum tests and tests following ingestion of suitable compounds. In any event, the blood tests do not specifically diagnose and distinguish NAFLD and NASH from other liver diseases. Most notably, the new serum tests (such as but not limited to FibroTest™) aim at correlation to fibrosis but have difficulties in detecting small changes in liver condition, which are needed for a genuine follow up. None of them have been adapted for use in routine clinical practice yet. They also suffer from the disadvantages of being performed at a central lab, thereby eliminating the economic benefit from the clinic.

Current imaging technologies, including ultrasound, Computed Tomography (CT), X-ray and Magnetic Resonance Imaging (MRI) cannot distinguish NAFLD from NASH. The new Fibroscan (ultrasound) test is not as effective with obese patients (a very significant (and growing) sector of the population), nor does it provide data on inflammation in the liver, nor does it provide information on actual liver function. Most imaging solutions (besides simple ultrasound which is useless for detecting fibrosis) do not exist at the standard medical clinic, and thus such solutions necessitate that the patients leave the physician's clinic, which has its drawbacks, such as location, long waiting period, lack of economic benefits, and more. A basic test in any of these devices (CT, X-ray and MRI) is expensive to highly expensive. Furthermore, there are other disadvantages to the previously used tests, such as the fact that they rarely give real time information about the organ function or status being observed. In some cases, such as in the case of blood tests for antibodies of bacterial infections, they give historic results which may have no current therapeutic relevance, since antibodies to a particular bacterium can remain in the body for up to 2 years from the date that the infection has been eradicated.

Moreover, the liver is an organ that has a very high metabolic capacity reserve. It is well known that a small part of a standard liver mass is sufficient to accomplish its physiological tasks. This poses a challenge when the liver has to be evaluated. Ideally the physician would like to get a quantitative evaluation of the liver mass, percentage of the cells that are functioning normally, or any other related parameter.

Furthermore, it is well known that the liver performs many tasks, and thereby it is difficult to assess all of its functions with a single test. Furthermore, there are many factors that result in high intra- and inter-patient variability. Finally, different disease etiologies may impact different functions of the liver.

The use of two breath tests has been proposed to provide a more accurate picture of the liver diseases. It has been demonstrated that accuracy of evaluation can be improved by using more than one substrate.

Methacetin, also known as N-(4-Methoxyphenyl)acetamide, p-Acetanisidine, p-Acetanisidine and [N-(4-methoxyphenyl)ethanamide] is a compound having the formula:

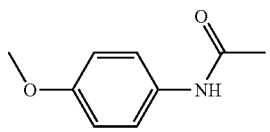

Methacetin may be utilized for the evaluation of liver functional capacity and/or the extent of liver injury. The biochemical basis for the evaluation of functional capacity is that the compound is metabolized by a cytochrome p450 enzyme expressed in normal liver cells (hepatocytes). Diseases of the liver that cause a loss in functional mass and/or impact the metabolic function of hepatocytes are associated with and may be correlated to a loss of capacity to metabolize methacetin.

One of the most common methods for determining the rate of metabolism of methacetin is to analyze the rate of metabolism of the methoxy group ($CH_3O$) of methacetin to carbon dioxide, which is excreted in exhaled breath. To distinguish the carbon dioxide derived from methacetin from all other sources of carbon dioxide, the methoxy group is labeled with $^{13}C$, a stable isotope of carbon. Thus, all the $CO_2$ derived from methacetin will contain $^{13}C(^{13}CO_2)$ in contrast to all other sources of $CO_2$, which will contain approximately 99% $^{12}C$, and 1% $^{13}C$, the naturally abundant isotope. Thus, the rate of excretion of $^{13}CO_2$ (normalized to $^{12}CO_2$) above background following the administration of methacetin-methoxy-$^{13}C$ indicates its rate of metabolism, which relates to the hepatic cell "health" and to the functional mass of the liver.

In common tests 75 mg of methacetin-methoxy$^{13}C$ is dissolved in 50-200 ml of water and taken orally, following which the excretion rate of $^{13}CO_2$ in exhaled air (breath testing {BT}) is determined at intervals of 15 minutes up to 2 hr. It has been reported that individuals with well-established cirrhosis have a statistically significant reduction in the rate of metabolism of methacetin, but considerable overlap exists between a group of volunteers having normal liver function and those with milder stages of potentially progressive liver disease and/or the degree of liver injury.

The probable causes for the wide variation in the methacetin breath testing within the normal population, which makes it difficult to distinguish it from the population with mild loss of functional capacity, need to be addressed and overcome as well as the intra-patient test variability. There is a need for a modified test that would enhance the usefulness of the methacetin in breath test for evaluating liver functional capacity and/or hepatic injury or health.

Octanoic acid, a medium-chain fatty acid and salts thereof undergo a metabolic process in the mitochondria of the liver cells. These compounds may be used in the assessment of hepatic mitochondrial β-oxidation. There is a need in the art for a test that would allow accurate evaluation of hepatic related conditions.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other advantages or improvements.

According to some embodiments, there are provided breath test devices and methods that may be used for the evaluation of liver functional and metabolic capacity or to assess liver heath and/or degree of liver injury.

In one embodiment, there is provided a method of evaluating a liver condition, the method includes measuring a change in isotope ratio of a metabolic product of methacetin, or a salt or a derivative of methacetin, in a subject's breath following administration of an isotope labeled methacetin, or a salt or a derivative thereof in a water solution, wherein the methacetin, or a salt or a derivative thereof is substantially dissolved in the solution.

In another embodiment, there is provided a method of evaluating a liver condition, the method includes on-line monitoring a metabolic product of methacetin, a salt or a derivative of methacetin, in a subject's breath after administering to the subject isotope labeled methacetin, a salt or a derivative thereof in water solution form. The method may further include monitoring $CO_2$ in breath. The method may further include analyzing at least one breath related parameter obtained by monitoring the metabolic product of methacetin in combination with at least one breath related parameter obtained by monitoring $CO_2$ in breath.

In yet another embodiment, there is provided a method of measuring the peak height and/or time of appearance of the peak and/or combination thereof, of a metabolic product of methacetin, a salt or a derivative of methacetin, in a subject's breath after administering to the subject isotope labeled methacetin, a salt or a derivative thereof.

In yet another embodiment, there is the method measuring the slope of rate of metabolization of methacetin, a salt or a derivative of methacetin, in a subject's breath after administering to the subject isotope labeled methacetin, a salt or a derivative thereof.

In yet another embodiment, there is provided a method of evaluating a liver condition, the method includes on-line monitoring a metabolic product of octanoic acid, a salt or a derivative of octanoic acid, in a subject's breath after administering to the subject isotope labeled octanoic acid, a salt or a derivative thereof.

In yet another embodiment, there is provided a method of measuring the peak height and/or time of appearance of the peak and/or combination thereof, of a metabolic product of octanoic acid, a salt or a derivative of octanoic acid, in a subject's breath after administering to the subject isotope labeled octanoic acid, a salt or a derivative thereof.

In yet another embodiment, there is providing a method of measuring the slope of rate of metabolization of octanoic acid, a salt or a derivative of octanoic acid, in a subject's breath after administering to the subject isotope labeled octanoic acid, a salt or a derivative thereof.

In another embodiment, there is provided a method of distinguishing between diagnosis of nonalcoholic steatohepatitis and nonalcoholic fatty liver, the method includes monitoring a metabolic product of octanoic acid, a salt or a derivative of octanoic acid, in a subject's breath after administering to the subject isotope labeled octanoic acid, a salt or a derivative thereof, wherein the method is based on the higher degree of metabolization in a subject having nonalcoholic fatty liver in comparison with a subject having nonalcoholic steatohepatitis and/or with a subject exhibiting normal liver function In another embodiment, there is provided a method of detecting abnormal beta-oxidation associated with insulin resistance or alcoholic liver disease or nonalcoholic liver fatty liver disease or metabolic syndrome, the method includes monitoring a metabolic product of octanoic acid, a salt or a derivative of octanoic acid, in a subject's breath after administering to the subject isotope labeled octanoic acid, a salt or a derivative thereof, wherein the method is based on the higher degree of metabolization in a subject having at least one of the conditions mentioned above in early stages in comparison with a subject having advanced/sever disease (wherein cells are damaged and/or mitochondrial damage has occurred) and/or in comparison with a subject exhibiting normal liver function.

In another embodiment, there is provided a method of evaluating a liver condition, the method includes continuously monitoring a metabolic product of octanoic acid, a salt or a derivative of octanoic acid, in a subject's breath after administering to the subject isotope labeled octanoic acid, a salt or a derivative thereof.

In another embodiment, there is provided a device for evaluating a liver condition, the device includes one or more sensors adapted to monitor on-line an isotope level of a metabolic product of labeled methacetin, or a salt or a derivative of methacetin in a subject's breath and a controller adapted to sample measurements of the one or more sensors at a continuous mode.

In another embodiment, there is provided a device for evaluating a liver condition, the device includes one or more breath sensors adapted to monitor an isotope level within a metabolic product of labeled octanoic acid, or a salt or a derivative of octanoic acid and a controller adapted to on-line sample measurements of the one or more sensors at a continuous mode.

In another embodiment, there is provided a kit for use in the evaluation of a liver condition, the kit includes isotope labeled methacetin, or a salt or a derivative thereof and water at least the amount sufficient to substantially dissolve the isotope labeled methacetin, or a salt or a derivative thereof, wherein the isotope labeled methacetin, or a salt or a derivative thereof and the water are not in direct contact with each other.

In another embodiment, there is provided a kit for use in the evaluation of a liver condition, the kit includes isotope labeled methacetin, or a salt or a derivative thereof in a water solution, wherein the labeled methacetin, or a salt or a derivative thereof is substantially dissolved in the water.

"Physiologic Noise"

In accordance with some embodiments, there is provided a method of evaluating a liver condition of a subject, the method includes computing a fluctuation parameter from a liver breath test based on at least one of a percentage dose recovery (PDR) curve and a delta over baseline (DOB) curve of an isotope labeled methacetin or a salt or a derivative thereof and evaluating at least one liver condition of the subject, based at least on the fluctuation parameter.

The method may further include the follow-up of the at least one liver condition by repeating, after a predetermined period of time, the steps of computing a fluctuation parameter from a liver breath test based on at least one of a percentage dose recovery (PDR) curve and a delta over baseline (DOB) curve of the isotope labeled methacetin or a salt or a derivative thereof; and evaluating the at least one liver condition of the subject, based at least on the fluctuation parameter. The predetermined period of time may be between 0.5 minutes and 4 hours. The predetermined period of time may be between 4 hours and 12 months.

In accordance with some embodiments, there is provided a method of evaluating a liver condition of a subject, the method includes computing a fluctuation parameter from a liver breath test based on at least one of a percentage dose recovery (PDR) curve and a delta over baseline (DOB) curve of an isotope labeled methacetin or a salt or a derivative thereof and computing an output indication related to at least one liver condition of the subject, based at least on the fluctuation parameter.

In accordance with some embodiments, there is provided a device for evaluating a liver condition of a subject, the device includes a processor adapted to compute a fluctuation parameter from a liver breath test based on at least one of a percentage dose recovery (PDR) curve and a delta over baseline (DOB) curve of an isotope labeled methacetin or a salt or a derivative thereof, wherein the fluctuation parameter is indicative at least one liver condition of the subject.

The processor may be further be adapted to follow-up of the at least one liver condition by re-computing, after a predetermined period of time, the fluctuation parameter from a liver breath test based on at least one of a percentage dose recovery (PDR) curve and a delta over baseline (DOB) curve of the isotope labeled methacetin or a salt or a derivative thereof. The predetermined period of time may be between 0.5 minutes and 4 hours. The predetermined period of time may be between 4 hours and 12 months.

The processor may further be adapted to compute an output indication related to at least one liver condition of the subject, based at least on the fluctuation parameter.

The isotope labeled methacetin, or a salt or a derivative thereof may include carbon-13, carbon-14, oxygen-18 or any combination thereof. The fluctuation parameter may be calculated by estimation of the noise in comparison to an essentially ideal smooth curve. A value of the fluctuation parameter being at or above a predetermined threshold may be indicative of at least one liver condition of the subject. A value of the fluctuation parameter being below a predetermined threshold may be indicative of a normal liver condition.

The liver condition may include liver related disease, malfunction, injury, transplantation, abnormality, fat accumulation, increased metabolism, decreased metabolism or a combination thereof.

Hepatic Impairment Score

In accordance with some embodiments, there is provided a method of evaluating a liver condition of a subject, the method includes computing a hepatic impairment score based at least on a breath test related parameter and on a demographic parameter.

The method may further include computing the trend of the hepatic impairment score. The method may further include displaying the hepatic impairment score, the trend of the hepatic impairment score, or both. The method may further include graphically displaying the hepatic impairment score, the trend of the hepatic impairment score, or both.

In accordance with some embodiments, there is provided a device for evaluating a liver condition of a subject, the device includes a processor adapted to compute a hepatic impairment score based at least on a breath test related parameter and on a demographic parameter. The processor may further be adapted to compute the trend of the hepatic impairment score. The device may further include a display adapted to show the hepatic impairment score, the prediction of disease using a threshold for the hepatic impairment score, probability of disease, or any combinations thereof. The device may further include a display adapted to graphically show the hepatic impairment score, the trend of the hepatic impairment score, or both.

The demographic parameter may include height, weight, age, gender, smoking habits, disease etiology, known information about complications, or any combination thereof. Computing a hepatic impairment score may further be based on a physiological noise related parameter, an appearance of an early peak, or both. The contribution of one or more parameters to the hepatic impairment score may depend on a value of the one or more parameters. Computing the hepatic impairment score may include averaging the values of the parameters. Computing the hepatic impairment score may be performed based on the medical significance of the parameters.

The hepatic impairment score may be in the range of 1 to 10. An increase in the hepatic impairment score may be indicative of a deterioration of the liver condition of the subject. A decrease in the hepatic impairment score may be indicative of an improvement in the liver condition of the subject. The hepatic impairment score may be computed based on an expert decision system.

The breath test related parameter may include isotope ratio of a metabolic product of methacetin, or a salt or a derivative of methacetin, in the subject's breath.

Composition of Methacetin

In accordance with some embodiments, there is provided a storage stable methacetin composition for use in a breath test, the composition comprising methacetin or a salt or derivative thereof substantially dissolved in water, wherein the composition is substantially free of anisidine. Substantially free of anisidine may include less than 1% anisidine. Substantially free of anisidine may include less than 0.2% anisidine. Anisidine may include p-anisidine. According to some embodiments, methacetin may be dissolved in purified water. The composition may be ready for oral administration. The composition may be adapted for storage at room temperature. The composition may include a single dose of methacetin. The composition may include a total aerobic microbial count of 100 cfu/ml or less. The composition may include a total yeast and mold count of 10 cfu/ml or less. The composition may be substantially free of E. Coli. The composition may be substantially free of preservatives. The composition may be substantially free of excipients that are adapted to inhibit methacetin decomposition. The composition may be prepared by dissolving methacetin in water at room temperature. The composition may be prepared by dissolving methacetin in water not exceeding a temperature of 55° C.

The composition may be maintained in a polymeric container.

The composition may be prepared by dissolving methacetin in water not exceeding a temperature of 55° C. and maintained in a polymeric container. The polymeric container may include polyethylene, polystyrene, polyester or any combination thereof.

The composition may be maintained in a glass container.

In accordance with some embodiments, there is provided a storage stable methacetin composition for use in a breath test, the composition includes methacetin or a salt or derivative thereof substantially dissolved in water, wherein the composition is substantially free of a by-product of methacetin decomposition. Substantially free of by product may include less than 1% by-product.

In accordance with some embodiments, there is provided a process for manufacturing a storage stable methacetin composition for use in a breath test, the process includes dissolving methacetin or a salt or derivative thereof in purified water to produce a storage stable methacetin composition, substantially free of anisidine. Substantially free of anisidine may include less than 1% anisidine. Substantially free of anisidine may include less than 0.2% anisidine. Anisidine may include p-anisidine.

The term "by-product of methacetin" may include any degradation and/or decomposition compound originated from methacetin or a salt or derivative thereof, such as but not limited to, anisidine. Anisidine may include p-anisidine. Anisidine may include m-anisidine. Anisidine may include o-anisidine.

The composition may be ready for oral administration. The composition may be adapted for storage at room temperature. The composition may include a single dose of methacetin. The composition may include a total aerobic microbial count of 100 cfu/ml or less. The composition may include a total yeast and mold count of 10 cfu/ml or less. The composition may be substantially free of E. Coli. The composition may be substantially free of preservatives. The composition may be substantially free of excipients that are adapted to inhibit methacetin decomposition. The process may include dissolving methacetin in water at room temperature. The process may include dissolving methacetin in water not exceeding a temperature of 55° C. The process may include maintaining the composition in a polymeric container. The process may include dissolving methacetin in water not exceeding a temperature of 55° C. and maintaining the composition in a polymeric container. The polymeric container may include polyethylene, polystyrene, polyester or any combination thereof.

The process may include maintaining the composition in a glass container.

The concentration of methacetin may decrease by no more than 1% after 26 weeks from manufacturing of the composition. The concentration of methacetin may decrease by no more than 1% after 26 weeks from manufacturing of the composition.

The composition may have a pH range of about 5.2 to 7.8. The composition may have a pH range of about 5.5 to 7.0. The composition may have a pH range of about 6.0 to 6.8. The pH may be maintained with or without an appropriate buffer. The composition may include about 0.05% methacetin.

Insulin Resistance

In accordance with some embodiments, there is provided a method of assessing insulin resistance in a subject, the method includes monitoring a metabolic product of octanoic acid, a salt or a derivative of octanoic acid, in a subject's breath after administering to the subject isotope labeled octanoic acid, a salt or a derivative thereof, and assessing insulin resistance in a subject based at least on the rate/amount of metabolism of the labeled octanoic acid, a salt or a derivative thereof.

BRIEF DESCRIPTION OF THE DRAWINGS

Exemplary embodiments are illustrated in the referenced figures and drawings. It is intended that the embodiments and figures disclosed herein are to be considered illustrative rather than restrictive.

DETAILED DESCRIPTION

Figure 1:
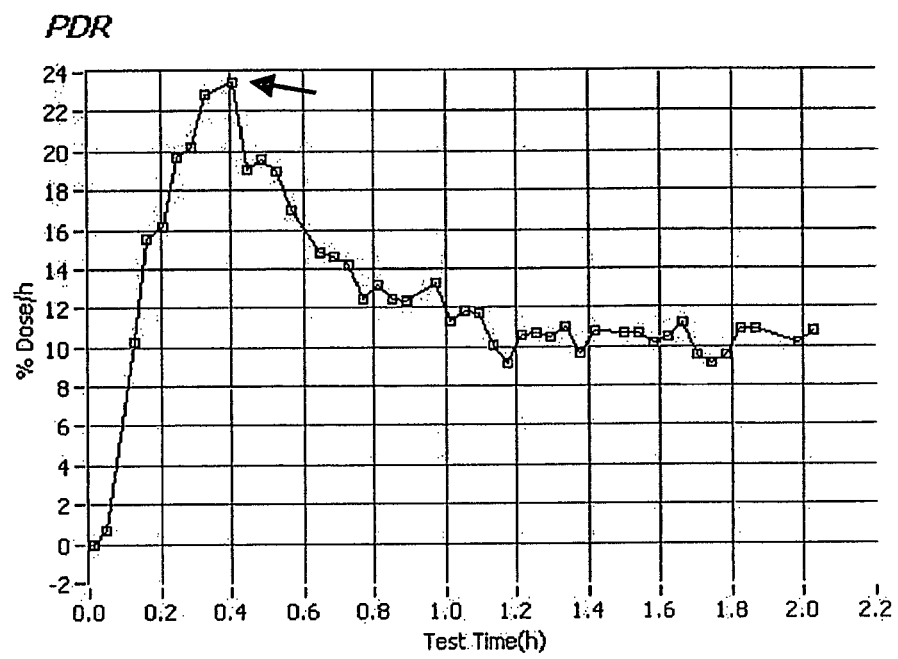
FIG. 1 shows a $^{13}$C-Methacetin Breath Test PDR (Percentage Dose Recovery) Curve, according to some embodiments.

While a number of exemplary aspects and embodiments have been discussed above, those of skill in the art will recognize certain modifications, permutations, additions and sub-combinations thereof. It is therefore intended that the following appended claims and claims thereafter introduced be interpreted to include all such modifications, permutations, additions and sub-combinations as are within their true spirit and scope.

In the following description, various aspects of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention.

In one embodiment, there is provided a method of evaluating a liver condition, the method includes measuring a change in isotope ratio of a metabolic product of methacetin, or a salt or a derivative of methacetin, in a subject's breath following administration of an isotope labeled methacetin, or a salt or a derivative thereof in a water solution, wherein the methacetin, or a salt or a derivative thereof is substantially dissolved in the solution.

The term "substantially dissolved" may include over 90% of methacetin, a salt or a derivative of methacetin dissolved in the solution. The term "substantially dissolved" may include over 99% of methacetin, a salt or a derivative of methacetin dissolved in the solution. The methacetin used herein may be any pre-made and/or pre-prepared solution of methacetin in a solvent, such as sterile or filtered water, with or without preservatives.

In another embodiment, there is provided a method of evaluating a liver condition, the method includes on-line monitoring of a metabolic product of methacetin, a salt or a derivative of methacetin, in a subject's breath after administering to the subject isotope labeled methacetin, a salt or a derivative thereof in water solution form. The subject may exhibit normal enzymatic (for example, liver related enzymes) activity. The method may further include monitoring $CO_2$ in breath. The method may further include analyzing at least one breath related parameter obtained by monitoring the metabolic product of methacetin in combination with at least one breath related parameter obtained by monitoring $CO_2$ in breath. The method may further include analyzing at least one breath related parameter obtained by monitoring the metabolic product of methacetin in combination with at least one physiological and/or medical parameter. The physiological and/or medical parameter may include age, gender, weight, height, blood related parameters, body mass index (BMI), waist circumference, medication therapy related parameter, or any combination thereof.

The method may further include the follow-up of liver condition, wherein the method may further include repeating, after a predetermined period of time, the step of on-line monitoring of a metabolic product of methacetin, a salt or a derivative of methacetin, in a subject's breath after administering to the subject isotope labeled methacetin, a salt or a derivative thereof.

In yet another embodiment, there is provided a method of measuring the peak height and/or time of appearance of the peak and/or combination thereof, of a metabolic product of methacetin, a salt or a derivative of methacetin, in a subject's breath after administering to the subject isotope labeled methacetin, a salt or a derivative thereof.

Reference is now made to FIG. 1, which shows a $^3$C-Methacetin Breath Test PDR (Percentage Dose Recovery) Curve, according to some embodiments. The curve depicts the rate of metabolism of $^{13}$C-Methacetin in % dose/hour as measured in breath. The peak of the curve (marked by the arrow) appears after 0.4 h (hours). The PDR peak height is approximately at 23.5% dose/hour.

In yet another embodiment, there is provided a method of evaluating a liver condition, the method includes measuring the slope of rate of metabolization, known in the art as percent dose recovery (PDR), of methacetin, a salt or a derivative of methacetin, in a subject's breath after administering to the subject isotope labeled methacetin, a salt or a derivative thereof.

In yet another embodiment, there is provided a method of evaluating a liver condition, the method includes on-line monitoring of a metabolic product of octanoic acid, a salt or a derivative of octanoic acid (such as, but not limited to, octanoate), in a subject's breath after administering to the subject isotope labeled octanoic acid, a salt or a derivative thereof.

In another embodiment, there is provided a method of distinguishing between diagnosis of nonalcoholic steatohepatitis and nonalcoholic fatty liver, the method includes monitoring a metabolic product of octanoic acid, a salt or a derivative of octanoic acid, in a subject's breath after administering to the subject isotope labeled octanoic acid, a salt or a derivative thereof, wherein the method is based on the higher degree of the metabolization in a subject having nonalcoholic fatty liver in comparison with a subject having nonalcoholic steatohepatitis and with a subject exhibiting normal liver function.

In another embodiment, there is provided a method of evaluating a liver condition, the method includes continuously monitoring a metabolic product of octanoic acid, a salt or a derivative of octanoic acid, in a subject's breath after administering to the subject isotope labeled octanoic acid, a salt or a derivative thereof. The method may be used in distinguishing between a nonalcoholic fatty liver and nonalcoholic steatohepatitis conditions in a subject. The method may further include monitoring $CO_2$ in breath. The method may further include analyzing at least one breath related parameter obtained by monitoring the metabolic product of octanoic acid in combination with at least one breath related parameter obtained by monitoring $CO_2$ in breath. The method may further include analyzing at least one breath related parameter obtained by monitoring the metabolic product of octanoic acid in combination with at least one physiological and/or medical parameter. The physiological and/or medical parameter may include age, gender, weight, height, blood related parameter, body mass index (BMI), waist circumference, medication therapy related parameter, or any combination thereof. The device may further include a processor adapted to analyze at least one breath related parameter obtained by monitoring isotope level of a metabolic product of the labeled methacetin, or a salt or a derivative of methacetin in combination with at least one breath related parameter obtained by monitoring $CO_2$ in breath.

In yet another embodiment, there is provided a method of measuring the peak height and/or time of appearance of the peak and/or combination thereof, of a metabolic product of octanoic acid, a salt or a derivative of octanoic acid, in a subject's breath after administering to the subject isotope labeled octanoic acid, a salt or a derivative thereof.

In yet another embodiment, there is provided a method of measuring the slope of rate of metabolization of octanoic acid, a salt or a derivative of octanoic acid, in a subject's breath after administering to the subject isotope labeled octanoic acid, a salt or a derivative thereof.

Figure 2:
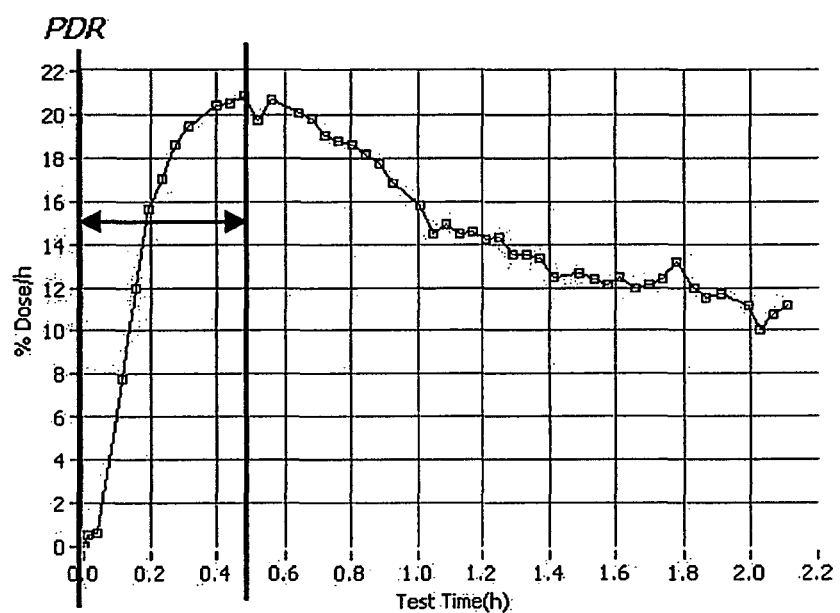
FIG. 2 shows a $^{13}$C-Octanoate Breath Test PDR (Percentage Dose Recovery) Curve, according to some embodiments.

Reference is now made to FIG. 2, which shows a $^{13}$C-Octanoate Breath Test PDR (Percentage Dose Recovery) Curve, according to some embodiments. The curve depicts the rate of metabolism of $^{13}$C-Octanoate in % dose/hour as measured in breath. The peak of the curve appears after 0.475 h (as shown by the arrow). The PDR peak height is approximately at 20.5% dose/hour.

Figure 3:
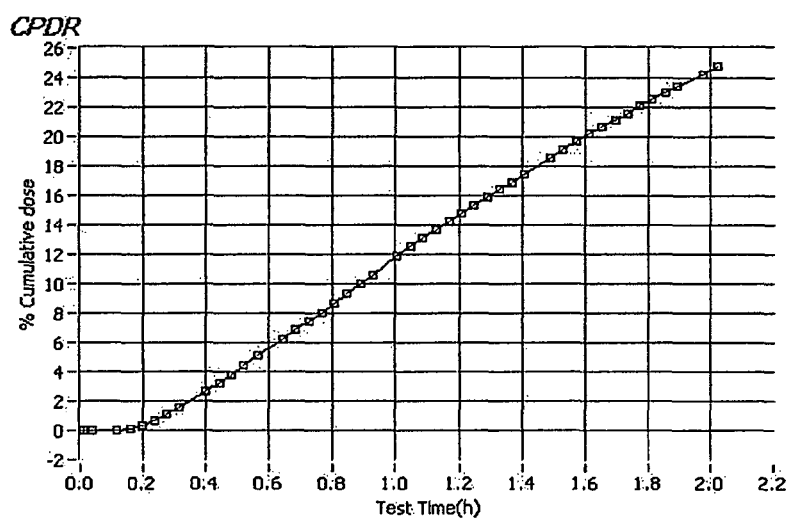
FIG. 3 shows a $^{13}$C-Methacetin/Octanoate Breath Test CPDR (Cumulative PDR) Curve, according to some embodiments.

FIG. 3 shows a $^{13}$C Octanoate Breath Test CPDR (Cumulative PDR) Curve, according to some embodiments. The curve depicts the total amount of labeled $^{13}C$ Octanoate metabolized in %, as measured in breath. Similar curves may be produced by measuring other substances, such as $^{13}C$ methacetin, or any other appropriate substance.

According to some embodiments, a breath test method is provided for distinguishing between levels of fibrosis in various liver diseases (such as HCV, NASH), the method may include evaluating the liver function by monitoring a metabolic product of methacetin in a subject's exhaled breath and detection of increased or induced metabolization in early stages of fibrosis. The levels of fibrosis may include 0, 1 and 2 levels. The fibrosis may be related to a liver disease.

According to some embodiments, a breath test method for the follow-up of liver condition is provided, the method may include performing a first evaluation of the liver function by monitoring a metabolic product of methacetin in a subject's exhale and performing a second evaluation, after a predetermined period of time, of the liver function by monitoring a metabolic product of methacetin in a subject's exhale. In another embodiment, the step of performing a second evaluation, after a predetermined period of time, of the liver function by monitoring a metabolic product of methacetin in a subject's exhale may be repeated a multiplicity of times.

According to some embodiments, there is provided a breath test method for detecting subjects having a liver condition and a normal enzymatic activity, the method may include evaluating the liver function of a subject by monitoring a metabolic product of methacetin in the subject's exhale.

According to some embodiments, a breath test method for distinguishing between NASH and NAFL in a subject suffering from NAFLD and/or to distinguish between healthy controls and NAFL or NASH patients is provided, the method may include evaluating the liver function by monitoring a metabolic product of octanoic acid, a salt, an ester, or a derivative thereof in a subject's exhale. In one embodiment, distinguishing between diagnosis of NASH and NAFL may be based on the increase of the liver function in a subject having NAFL in comparison to a subject having NASH and healthy subjects.

According to some embodiments, any breath test method for evaluating liver condition, liver function, metabolic capacity and/or to assess liver heath and/or degree of liver injury, provided herein may further include administering to the subject a test meal that may challenge the liver in a way that the "essentially all" liver has to function to a normal extent to metabolize the test meal rapidly and effectively.

According to some embodiments, any breath test method for evaluating liver condition, liver function, metabolic capacity and/or to assess liver heath and/or degree of liver injury provided herein may further include monitoring $CO_2$ in breath, for example, by capnography. This may enable minimizing test length and variations in metabolic rate and/or $CO_2$ production that would introduce non-relevant variables to liver test evaluation.

In another embodiment, the disclosure relates to a method for evaluating liver functional capacity and/or health. In another embodiment, the disclosure relates to a method for testing liver functional capacity. In another embodiment, the disclosure relates to a method for monitoring liver functional capacity. In another embodiment, the disclosure relates to a method for conducting a follow-up of liver functional capacity.

In another embodiment, a method is provided for evaluating liver functional capacity and/or health by analyzing breath test parameters that provide quantitative presentation of the dynamic of the liver response. In another embodiment, the incline slope following administration of substrate, the peak time, the peak height/peak time, and other appropriate parameters may be calculated and provided.

In another embodiment, there is provided a device for evaluating a liver condition, the device includes one or more sensors adapted to monitor on-line an isotope level of a metabolic product of labeled methacetin, or a salt or a derivative of methacetin in a subject's breath and a controller adapted to sample measurements of the one or more sensors at a continuous mode. The device may be used for distinguishing between levels of fibrosis.

In another embodiment, there is provided a device for evaluating a liver condition, the device includes one or more breath sensors adapted to monitor an isotope level within a metabolic product of labeled octanoic acid, or a salt or a derivative of octanoic acid and a controller adapted to on-line sample measurements of the one or more sensors at a continuous mode. The device may be used in distinguishing between a nonalcoholic fatty liver and nonalcoholic steatohepatitis conditions in a subject.

Any device disclosed herein may be adapted to sample measurements of the one or more sensors at a continuous mode, while the subject is coupled to the device during breath sampling. The term "coupled to the device" may include coupling through a nasal cannula. The device may be adapted to automatically collect and analyze breath samples.

Any device disclosed herein may further include one or more breath sensors, such as capnography sensors, adapted to monitor $CO_2$ in breath. The device may further include a processor adapted to analyze at least one breath related parameter obtained by monitoring isotope level within a metabolic product of a labeled substance, such as methacetin and/or octanoic acid, or any salt or derivative thereof, in combination with at least one breath related parameter obtained by monitoring $CO_2$ in breath. The processor may correct for changes in $CO_2$ exhaled/production of a subject throughout the breath test.

Any device disclosed herein may further include a processor adapted to analyze at least one breath related parameter obtained by monitoring the metabolic product of a substance, such as methacetin and/or octanoic acid or any salt or derivative thereof, in combination with at least one physiological and/or medical parameter. Physiological and/or medical parameters may include, for example, age, gender, weight, height, blood related parameter, body mass index (BMI), waist circumference, medication therapy related parameter, any combination thereof, or any other relevant parameter.

According to some embodiments, there is provided an improved breath test analyzer which provides accurate results on-site in times of the order of minutes, and which may be capable of implementation as a low cost, low volume and weight, portable instrument. According to some embodiments, the device may be sufficiently sensitive to enable it to function on-line by continuously collecting and analyzing multiple samples of the patient's breath from the beginning of the test, and processing the outputs in real time, such that a definitive result is obtained within a short period of time, such as, but not limited to, in the order of a few minutes.

Such a breath test analyzer may be suitable for the detection of various disorders such as, but not limited to, metabolic or organ malfunctions, and since it can provide results in real time without the need to send the sample away to a special testing center or central laboratory, it can be used to provide diagnostic information to the patient in the context of a single visit to a physician's office, or at any other point of care in a health care facility.

In another embodiment, there is provided a kit for use in the evaluation of a liver condition, the kit includes isotope labeled methacetin, or a salt or a derivative thereof and water at least the amount sufficient to substantially dissolve the isotope labeled methacetin, or a salt or a derivative thereof, wherein the isotope labeled methacetin, or a salt or a derivative thereof and the water are not in direct contact with each other. The kit may further include means for combining the isotope labeled methacetin, or a salt or a derivative thereof and the water.

In another embodiment, there is provided a kit for use in the evaluation of a liver condition, the kit includes isotope labeled methacetin, or a salt or a derivative thereof in a water solution, wherein the labeled methacetin, or a salt or a derivative thereof is substantially dissolved in the water.

In one embodiment, a water-soluble form of methacetin, a salt or a derivative thereof is provided. In another embodiment, the water-soluble form of methacetin may facilitate absorption of methacetin in comparison to non-treated methacetin. In another embodiment, the absorption of methacetin may be active or passive.

The term "form of methacetin" may be, according to some embodiments, a composition, complex, mixture, combination, compound, formulation, inclusion complex, and the like, that includes methacetin.

The term "water-soluble form of methacetin" may include, according to some embodiments, a form of methacetin having larger water solubility than methacetin alone.

In another embodiment, the disclosure also relates to pharmaceutical compositions, which may include a predetermined amount of water-soluble form of methacetin, a salt or a derivative thereof, together with one or more pharmaceutically acceptable carriers or excipients.

In one embodiment there is further provided a method for the preparation of a water-soluble form of methacetin, a salt or a derivative thereof, the method may include dissolving a complexing agent in water and adding methacetin, a salt or a derivative thereof.

In another embodiment, the disclosure relates to use of the water-soluble form of methacetin, a salt or a derivative thereof for the preparation of a pharmaceutical composition for use in testing liver functional capacity and/or health.

According to some embodiments, detecting, monitoring, distinguishing, evaluating, measuring, differentiating, quantifying, and the like, as referred to herein, may be accomplished by any of the apparatuses, breath collection systems, analyzer units, calibration devices, algorithms and methods described herein, and/or, as exemplary embodiments, by any of the apparatuses, breath collection systems, analyzer units, calibration devices, algorithms and methods disclosed in U.S. Pat. Nos. 6,186,958, 6,491,643 and 6,656,127, 7,488,229 and 6,491,643.

More specifically, such devices, apparatuses and methods can be used for a metabolic liver function test, which could be utilized to assess liver function. According to some embodiments, by administering a specific compound orally or intravenously, a compound is directly metabolized or removed by the liver from the blood and metabolized, and a metabolic product is then released into the blood and excreted in the bile, urine, saliva, or exhaled breath. Methods according to some embodiments may include measuring the amount of the administered product that remains in serum over time or the amount of metabolic product that is produced and/or the rate at which this product is excreted, and provides a potentially accurate measure of hepatic metabolic function. Several compounds have been utilized to measure hepatic metabolic function in this manner including indocyanine green, galactose, aminopyrine, caffeine, lidocaine, phenylalanine and Methacetin[N-(4-Methoxy-phenyl)acetamide]. Previous studies of the hepatic metabolism of lidocaine to monoethylglycinexylodide (MEGX) have demonstrated that: a. declined metabolism was apparent with increasing liver fibrosis and with worsening stages of cirrhosis, b. improved metabolism was apparent with successful treatment of the underlying liver disease, and c. an accurate prediction of which patients with stable cirrhosis awaiting liver transplantation were at risk to develop future hepatic decompensation. The liver tests are aimed at the patient population with acute or chronic liver disease. This includes persons infected with hepatitis C, patients with NASH or alcoholic related liver disease, liver transplant patients, and more. By the administration of a substrate that is exclusively (or almost exclusively) metabolized by the liver, at least during the breath testing procedure, liver function can be analyzed.

In accordance with one embodiment, there is provided a breath test analyzer, including a very sensitive gas analyzer, capable of measuring a ratio of two chemically identical gases with different molecular weights. The gas analyzer is capable of measuring small quantities of isotopically labeled gas, which may be present in the breath of a patient.

There are a number of different operational modes for each type of test for such a breath analyzer, in which the analysis is performed on-line in real time while a patient is continuing to provide breath for subsequent analyses. In a common mode of operation, a breath test analyzer senses exhaled breath of a patient before ingestion of an isotopically labeled substance and analyzes the exhaled breath of a patient for the percentage of isotopically labeled gas from the total exhaled gas of that composition, in order to obtain a baseline reading. At least one more similar analysis after ingestion of an isotopically labeled substance, provides an indication of a medical condition within a time period. The time period is defined to be the last sensing, which is between the first sensing of the patient's exhaled breath and the second sensing. This feature differentiates these breath analyzers from all the rest, since it provides analyses in a very short time period.

In an alternative mode of operation, the analyses are made successively at times after ingestion of an isotopically labeled substance, and before the end of production of the isotopically labeled by-products of the substance, and the analyzer performs comparisons of the change from sample to sample of the percentage of the isotopically labeled gas in the total exhaled gas of that composition, and thereby provides an indication of a medical condition as soon as the detected change in gas composition percentage permits it, and before the end of production of the isotopically labeled by products of the substance.

In accordance with some embodiments, there are at least two modes of analyzing the breath samples. The analyzer can either perform its analysis on individual exhaled breaths, or, as stated herein, it can perform its analysis on-line on multiple samples of the patient's breath, continuously collected from the patient. It is further described an analyzer wherein the breaths of a patient are exhaled into a reservoir for collection, called a breath collection chamber, and later transferred by various methods to the sample measurement chamber. An advantage of the method described therein, is that the analyzer draws an averaged sample of breath for measurement, instead of individual breaths, thereby increasing accuracy. Another advantage is that it is possible to collect only the plateau parts of multiple breaths for analysis (the relevant portion of the exhale).

In accordance with a further embodiment, there is provided a breath test analyzer, which analyzes a first exhaled breath of a patient and a second exhaled breath of the patient for isotope labeled products generated in a patient's body after ingestion by the patient of an isotope labeled substance. By performing an analysis of a patient's first breath and second breath, at least the second breath being exhaled following patient's ingesting the substance, the analyzer provides an indication of a medical condition within a time period following the exhalation of the second breath, which is less than the difference in time between the exhalation of the first breath and the exhalation of the second breath.

In accordance with a further embodiment, a breath test analyzer as described herein includes a breath analysis chamber, a breath inlet conduit for conveying exhaled gas from a patient to the breath analysis chamber; and a gas analyzer operative to analyze gas in the breath analysis chamber and to conduct the first analyzing of gas exhaled by the patient's first breath and the second analyzing of the patient's second breath, at least the second breath being exhaled following ingestion by the patient of an isotope labeled substance.

Furthermore, for those embodiments which analyze samples collected from exhaled breaths of a patient, it is understood that the analyzer also incorporates a breath collection chamber, which may be a separate chamber, or part of the breath inlet conduit, or part of the breath analysis chamber. In the latter case, the analysis of the gas sample effectively takes place in the breath collection chamber.

In accordance with further embodiments, there is provided a breath test analyzer as described herein, and wherein the first breath of a patient is exhaled prior to ingestion of an isotopically labeled substance, and the second breath of a patient is exhaled following ingestion of the isotopically labeled substance.

In accordance with further embodiments, there is provided a breath test analyzer as described herein, and wherein both of the first and second breaths of a patient are exhaled following a patient's ingestion of the isotopically labeled substance.

In accordance with further embodiments, there is provided a breath test analyzer that analyzes a breath of a patient for an isotope labeled product generated in the body of a patient after ingestion of an isotope labeled substance. The analyzer provides an indication of a medical condition existent in the patient, by analyzing at least two successive samples of the patient's breath, wherein the at least two successive samples of the patient's breath include at least one later sample exhaled following analysis of at least one earlier sample.

In accordance with a further embodiment, there is provided a breath test analyzer as described herein and including a breath analysis chamber, a breath inlet conduit for conveying exhaled gas from a patient to the breath analysis chamber, and a gas analyzer operative to analyze gas in the breath analysis chamber and to conduct analyses of the at least two successive samples of the patient's breath, wherein the at least two successive samples of the patient's breath include at least one later sample exhaled following analysis of at least one earlier sample.

In accordance with another embodiment, there is provided a breath test analyzer which analyzes a patient's exhaled breath before and after a product of an isotope labeled substance ingested by the patient could be detected in the patient's breath, a first analysis of the patient's exhaled breath, which takes place prior to the product being detectable in the patient's breath, and a second analyzing of the patient's exhaled breath taking place once the product could be detectable in the patient's breath. The analyzer provides an indication of a medical condition within a time period following the exhalation of the second breath, which is less than the difference in time between the exhalation of the first breath and the exhalation of the second breath.

There is further provided, in accordance with other embodiments, a breath test analyzer which monitors on-line a first exhaled breath of a patient and a second or any of the following exhaled breath of the patient for the products of an isotope labeled substance ingested by the patient while the patient is coupled on-line to the device, or monitors the above-mentioned exhaled breath and provides an indication of a medical condition while the patient is coupled to the device, or is continuously breathing into the device on-line. The patient whose breath is being analyzed may be on-line coupled to the device continuously from the monitoring of the first exhaled breath to the monitoring of the second or any of the following exhaled breath.

Further provided in accordance with an embodiment, is a breath test analyzer as described herein, including a breath analysis chamber, a breath inlet conduit for conveying exhaled gas from a patient to the breath analysis chamber, and a gas analyzer operative to analyze gas in the breath analysis chamber while the patient is on-line coupled to the device.

There is even further provided, in accordance with another embodiment, a breath test analyzer as described herein and including a breath analysis chamber, a breath inlet conduit for conveying exhaled gas from a patient to the breath analysis chamber, and a gas analyzer operative to analyze gas in the breath analysis chamber and to provide an indication of a medical condition while the patient is coupled to the device.

There is also provided, in accordance with another embodiment, a breath test analyzer as described herein and including a breath analysis chamber, a breath inlet conduit for conveying exhaled gas from a patient to the breath analysis chamber, and a gas analyzer operative to analyze gas in the breath analysis chamber and to provide an indication of a medical condition while the patient is breathing into the device.

In accordance with still another embodiment, there is provided a breath test analyzer as described herein and wherein the patient is coupled to a disposable breath input device.

In accordance with yet another embodiment, there is provided a medical sample analyzer which analyzes samples taken from a patient, and wherein either the taking or the analyzing of the samples is terminated automatically at a point in time determined by the results of the analyzing of the samples.

In accordance with even another embodiment, there is further provided a breath test analyzer which analyzes samples of a patient's breath for isotope labeled products generated in the patient's body after ingestion by the patient of an isotope labeled substance, and wherein either the taking or the analyzing of the samples is terminated automatically at a point in time determined by the results of the analyzing of samples.

There is also provided, in accordance with another embodiment, a medical sample analyzer as described herein, which analyzes samples taken from a patient and including a sample input port for receiving samples taken from the patient and an analyzing apparatus for analyzing the samples, and wherein the analyzing is terminated automatically at a point in time determined by the results of the analyzing of the samples.

There is further provided, in accordance with another embodiment, a breath test analyzer as described herein and including a breath analysis chamber, a breath inlet conduit for conveying exhaled gas from a patient to the breath analysis chamber, and a gas analyzer operative to analyze gas in the breath analysis chamber and wherein the analyzing of samples from the patient is terminated automatically at a point in time determined by the results of the analyzing of the samples.

In accordance with another embodiment, there is further provided a breath test analyzer as described herein, and wherein the gas analyzer includes a gas discharge lamp, or an infra-red source which emits a discontinuous spectrum.

In accordance with another embodiment, there is provided a breath test analyzer as described herein, and wherein the results of the analyzing of successive samples are fitted to a curve, and an indication of a medical condition in a patient is determined by inspecting the derivative of the curve.

In accordance with another embodiment, there is further provided a method of breath testing which analyzes a first exhaled breath of a patient and a second exhaled breath of the patient for isotope labeled products generated in the patient's body after ingestion by the patient of an isotope labeled substance, and including the steps of performing a first analysis of the patient's first breath, subsequently performing a second analysis of the patient's second breath, at least the second breath being exhaled following the patient's ingesting the substance, and providing an indication of a medical condition within a time period following exhalation of the second breath, which is less than the difference in time between exhalation of the first breath and exhalation of the second breath.

Further provided, in accordance with another embodiment, is a method of breath testing which analyzes a patient's exhaled breath for the product of an isotope labeled substance ingested by the patient, and including the steps of performing a first analyzing of the patient's exhaled breath prior to the product being detectable in the patient's breath, performing a second analyzing of the patient's exhaled breath once the product is detectable in the patient's breath, and providing an indication of a medical condition within a time period following the exhalation of the second breath, which is less than the difference in time between the exhalation of the first breath and the exhalation of the second breath.

Furthermore, whereas all of the above-mentioned embodiments have been described for breath analyzers which analyze a first exhaled breath of a patient and a second exhaled breath of the patient, it is understood that the operation of these embodiments are equally valid for a breath analyzer which analyzes a first sample collected from at least a first exhaled breath of a patient, and a second sample collected from at least a second exhaled breath of a patient.

Furthermore, this breath test analyzer is also sufficiently small that it can easily be accommodated in the office of a physician, and its cost is also sufficiently low that its use in such an environment can be economically justified.

A specific substance, compound and/or composition may be administered (for example, for the purpose of breath tests), orally, intravenously, nasally, transdermally, rectally, in eye drops, using an implemented device, or in any other appropriate form. However, it should be clear to one of skill in the art that any method of administering a substance into a subject, either known today or to be developed in the future, may be applicable to the present invention and is contemplated. The substance (for example, a compound) may be directly metabolized or removed by the liver, and a metabolic product is then released into the blood and excreted in the bile, urine, saliva, or exhaled breath. Measuring the amount of the administered product that remains in serum over time or the amount of metabolic product that is produced and/or the rate, at which this product is excreted, provides a potentially accurate measure of hepatic metabolic function.

According to some embodiments, breath tests may utilize $^{13}C$-labeled substrates providing a safe and non-invasive means for measuring hepatic metabolism. $^{13}C$ is a stable, non-radioactive isotope, which can be incorporated into a specific location within the molecule of a test substrate so that after metabolization by the liver into $^{13}CO_2$, it would be released. The $^{13}C$-compound may be administered orally, rapidly absorbed and metabolized by the liver, and then the $^{13}CO_2$ may be measured in exhaled breath within a predetermined period of time.

In one embodiment, the predetermined period of time, as referred to herein, may be 10-60 minutes. In another embodiment, the predetermined period of time may be 0.5-5 minutes. In another embodiment, the predetermined period of time may be 10-120 minutes. In another embodiment, the predetermined period of time may be 1-10 minutes. In another embodiment, the predetermined period of time may be 5-15 minutes. In another embodiment, the predetermined period of time may be 10-30 minutes. In another embodiment, the predetermined period of time may be 15-45 minutes. In another embodiment, the predetermined period of time may be 30-60 minutes. In another embodiment, the predetermined period of time may be 1-2 hours. In another embodiment, the predetermined period of time may be 1.5-3 hours.

In another embodiment, the predetermined period of time may be 3-4 hours.

In one embodiment, the predetermined period of time may vary between measurements. Hepatic metabolism of the compound may be assessed by measuring the ratio of $^{13}C:^{12}C$ in exhaled breath. According to some embodiments, detecting, differentiating and quantifying $^{13}C$ and $^{12}C$, in exhaled $CO_2$ may be accomplished by any of the apparatuses, breath collection systems, analyzer units and methods described herein, and/or, as exemplary embodiments, by any of the apparatuses, breath collection systems, analyzer units, calibration devices, algorithms and methods disclosed in U.S. Pat. Nos. 6,186,958, 6,491,643 and 6,656,127, 7,488,229 and 6,491,643. According to some embodiments, portable office-based system may continuously sense and collect exhaled breath and analyzes $CO_2$ in on-line in real-time through a nasal cannula worn by the patient, and may enable evaluation of liver function in real time, thereby providing a follow-up method in clinical hepatology. According to some embodiments, such a test has been designed to provide a sensitivity and accuracy required for accurate detection of clinically relevant variations as small as 1/1000 in the $^{13}CO_2/^{12}CO_2$ ratio.

Though carbon-13 is the most commonly used isotopic replacement atom in such breath tests, according to some embodiments, other atoms may be used instead of or in addition to carbon-13, including but not limited to, carbon-14, nitrogen-15 and oxygen-18 and others.

According to one embodiment, liver function or liver mass or liver health or liver injury evaluation may be performed by monitoring the P450 enzyme activity, or any other appropriate means. In another embodiment, liver disease severity and detoxification activity may be evaluated by means of the ingestion of $^{13}C$-labeled aminopyrine, methacetin, caffeine citrate or any other appropriate means (depending on the specific function being tested) and breath detection of an increased level of $^{13}CO_2$.

According to one embodiment, the quantification of functional liver mass by means of the ingestion of $^{13}C$-labeled galactose, and breath detection of an increased level of $^{13}CO_2$ may be performed.

Evaluation of the Methacetin breath test for quantifying liver function indicates that some of the intra- and inter-variability previously reported, which makes it difficult to distinguish the normal population from those with liver disease, can be attributed to determinants that affect the rate of intestinal absorption and consequently the amount of methacetin that is taken up by the liver per unit time. In these instances, the maximum rate of production of $^{13}CO_2$ may be affected by rates of intestinal absorption and not only by the maximum rates of metabolism by the liver, thus yielding falsely low values in the normal population. This applies to the dynamic response as well.

According to some embodiments, measurement of hepatic mitochondrial activity may be evaluated by means of the ingestion of $^{13}C$-labeled octanoic acid, and breath detection of an increased level of $^{13}CO_2$.

According to some embodiments, hepatic mitochondrial function efficiency may be evaluated by means of the ingestion of $^{13}C$-labeled ketoisocaproic acid, and breath detection of an increased level of $^{13}CO_2$.

Diagnosis of Fibrosis Liver Disease

According to some embodiments, a breath test method is provided for distinguishing between levels of fibrosis, for example, 0, 1 and 2 levels of fibrosis liver disease (for example, but not limited to, based on METAVIR, ISHAK or Knodell or Brunt fibrosis scores), the method may include evaluating the liver function by monitoring a metabolic product of methacetin in a subject's exhale. In another embodiment, a breath test method is provided for monitoring the level of fibrosis liver disease based on the increase of the liver function in subjects while fibrosis is progressing from level 0 to level 1, the method may include performing a first evaluation of the liver function by monitoring a metabolic product of methacetin in a subject's exhale and performing a second evaluation, after a predetermined period of time, of the liver function by monitoring a metabolic product of methacetin in a subject's exhale. In another embodiment, the step of performing a second evaluation, after a predetermined period of time, of the liver function by monitoring a metabolic product of methacetin in a subject's exhale may be repeated a multiplicity of times.

In one embodiment, the term "multiplicity" may refer to any number higher than 1. In another embodiment, the term "multiplicity" may refer to any number higher than 2. In another embodiment, the term "multiplicity" may refer to any number higher than 3.

In another embodiment, distinguishing between levels 0, 1 and 2 of fibrosis liver disease is based on the increase of the liver function in subjects having level 1 fibrosis in comparison to subjects having levels 0 and 2. In another embodiment, the subject may be suffering from a chronic hepatitis C, B or NAFL/NASH or any other type of chronic liver disease.

In yet another embodiment, the methacetin breath test is used to detect cirrhosis by detecting a group of patients with fibrosis grade 5 in Ishak fibrosis scores (which is sometimes classified as incomplete cirrhosis in histology) or grade 6 in Ishak fibrosis scores (clear cirrhosis in histology) using one threshold and applying a second threshold for detection of grade 6 only.

In yet another embodiment, the methacetin breath test is used to provide a score that provides a probability for suffering from a certain level of fibrosis and/or inflammation.

In another embodiment, distinguishing between levels 0, 1 and 2 of fibrosis liver disease is based on a combination of data from methacetin and octanoic acid breath tests, or their derivatives.

In yet another embodiment, distinguishing between NAFL and NASH disease is based on a combination of data from breath tests of methacetin and octanoic acid, or its derivatives, performed on the same patient on different days.

In yet another embodiment, distinguishing between normal and NAFL or between normal and NASH disease is based on a combination of data from breath tests of methacetin and octanoic acid, or their derivatives, performed on the same patient on different days. For example, if a patient presents octanoate metabolization level in the normal range but methacetin metabolization level lower than in the normal range this would indicate that the patient suffers from NASH.

In yet another embodiment, distinguishing between NAFL and NASH disease is based on a combination of data from breath tests of methacetin and octanoic acid, or its derivatives, performed on the same patient on different days and other medical information (such as, age, BMI).

In yet another embodiment, distinguishing between normal and NAFL or between normal and NASH disease is based on a combination of data from breath tests of methacetin and octanoic acid, or their derivatives, performed on the same patient on different days and other medical information (such as, age, BMI)

Follow-Up of a Liver Condition

According to some embodiments, a breath test method for the follow-up of a liver condition is provided, the method may include performing a first evaluation of the liver function by monitoring a metabolic product of methacetin in a subject's exhale and performing a second evaluation, after a predetermined period of time, of the liver function by monitoring a metabolic product of methacetin in a subject's exhale. In another embodiment, the step of performing a second evaluation, after a predetermined period of time, of the liver function by monitoring a metabolic product of methacetin in a subject's exhale may be repeated a multiplicity of times. In another embodiment, the follow-up may include a follow-up of the progression of a liver condition. In another embodiment, the follow-up may include follow-up of the deterioration of a liver condition, for example, but not limited to, subjects suffering from acute and/or chronic liver disease. In another embodiment, the follow-up may include a follow-up of the improvement of a liver condition.

In another embodiment, the term "liver condition" may refer to any liver related disease, malfunction, injury, transplantation, abnormality, fat accumulation, increased metabolism, decreased metabolism, and others.

Assessment of Disease Activity and Follow-Up in Patients with Fatty Liver Diseases According to some embodiment, a score based on octanoate breath test is derived to correlate with histology-based activity score such as, for example, the NAS score that is used to grade activity in NAFLD patients using standard statistical regression techniques (Additional information regarding NAS score may be found, for example in Kleiner D. E., et. al. Nonalcoholic Steatohepatitis Clinical Research Network. Design and validation of a histological scoring system for nonalcoholic fatty liver disease. Hepatology. 2005 June; 41(6):1313-21; incorporated herein by reference in their entirety.

According to some embodiments, a breath test method for the follow-up of a liver condition in NAFLD patients is provided, the method may include performing a first evaluation of the liver function by monitoring a metabolic product of octanoate in a subject's exhale and performing a second evaluation, after a predetermined period of time, of the octanoate metabolisation by monitoring a metabolic product of octanoate in a subject's exhale. In another embodiment, the step of performing a second evaluation, after a predetermined period of time, of the liver function by monitoring a metabolic product of octanoate in a subject's exhale may be repeated any multiplicity of times. In another embodiment, the follow-up may include a follow-up of the changes in the activity of the diseases. In another embodiment, the follow-up may include using the octnaote breath test as a "surrogate marker" or "end point" for management of NAFLD patients.

According to some embodiments, a breath test method for the follow-up of a liver condition in patients with alcoholic liver disease (ALD) is provided, the method may include performing a first evaluation of the liver function by monitoring a metabolic product of octanoate in a subject's exhale and performing a second evaluation, after a predetermined period of time, of the octanoate metabolisation by monitoring a metabolic product of octanoate in a subject's exhale. In another embodiment, the step of performing a second evaluation, after a predetermined period of time, of the liver function by monitoring a metabolic product of octanoate in a subject's exhale may be repeated any multiplicity of times. In another embodiment, the follow-up may include a follow-up of the changes in the activity of the diseases. In another embodiment, the follow-up may include using the octnaote breath test as a "surrogate marker" or "end point" for management of ALD patients.

Screening Subjects Having a Liver Condition

According to some embodiments, a breath test method for detecting subjects having a liver condition and a normal enzymatic activity, the method may include evaluating the liver function of a subject by monitoring a metabolic product of methacetin in the subject's exhale. In another embodiment, the method may further include performing a second evaluation, after a predetermined period of time, of the liver function by monitoring a metabolic product of methacetin in a subject's exhale. In another embodiment, the step of performing a second evaluation, after a predetermined period of time, of the liver function by monitoring a metabolic product of methacetin in a subject's exhale may be repeated a multiplicity of times. In another embodiment, normal enzymatic activity may include normal alanine aminotransferase values.

Diagnosis of NAFL Vs. NASH

Octanoic acid, a medium-chain fatty acid, and salts thereof, are a reliable substrate to assess hepatic mitochondrial β (beta)-oxidation by means of a breath test. Hepatic mitochondrial beta-oxidation plays a role in the pathogenesis of NAFLD. Increased lipid peroxidation and/or hepatic cell injury and/or impairment in metabolic cycles can differentiate between NASH and NAFL and between these conditions and a healthy liver. Therefore, there is a potential solution for the need in the art for a test that would allow the differentiation between NASH and NAFL and those who are healthy, based on evaluation of hepatic mitochondrial beta-oxidation.

According to some embodiments, a breath test method for distinguishing between NASH and NAFL in a subject suffering from NAFLD is provided, the method may include evaluating the liver function/health by monitoring a metabolic product of octanoic acid, a salt, an ester or a derivative thereof in a subject's exhale. In one embodiment, distinguishing between diagnosis of NASH and NAFL may be based on the increase of the liver function or metabolization of octanoic acid or a derivative thereof in a subject having NAFL in comparison to a subject having NASH.

In another embodiment, NAFLD may be diagnosed prior to distinguishing between diagnosis of NASH and NAFL. In another embodiment, high probability of NAFLD may be indicated by ultrasonic means. In another embodiment, liver diseases other than NAFLD may be excluded prior to distinguishing between diagnosis of NASH and NAFL. In another embodiment, liver diseases other than NAFLD may be excluded prior to distinguishing between diagnosis of NASH and NAFL by a blood test. In another embodiment, the blood test may include a biochemical serum test. In another embodiment, use of other characteristics of individual patients are combined with breath test data such as body mass index (BMI), specific blood parameters, blood pressure, waist circumference, age, gender, and so forth, to improve evaluation of liver health. In another embodiment NAFL and/or NASH can be differentiated from patients with healthy liver.

In yet another embodiment, elevated OBT is used as an aid in diagnosis of simple non-alcoholic fatty liver (NAFL).

In yet another embodiment, elevated OBT is used as an aid in diagnosis of simple alcoholic fatty liver (AFL).

A Modified Breath Test

As disclosed herein, isotope labeled octanoic acid, a salt or a derivative of octanoic acid (such as, but not limited to, octanoate) may be used to determine liver condition(s).

Fatty acids (such as octanoate) metabolization and release of the $^{13}C$ carbon in a form of $^{13}CO_2$ requires multiple steps including beta-oxidation, generation of $^{13}C$ labeled Acetyl-CoenzymeA (AcCoA) and subsequently release of the $^{13}C$ carbon in the Tricarboxylic acid cycle (TCA) cycle. Improper TCA function may lead to accumulation of AcCoA. It is known that alternative pathways exist for AcCoA, which result in ketone bodies generation or lipogenesis, which would not be detected in a breath test.

The percentage of the labeled octanoate salt that continues in the TCA cycle versus the percentage of the labeled octanoate that goes to generation of ketone bodies may depend on the physiological condition of the subject. For example, in starving/fasting conditions, oxalacetic acid may be needed (as it is used by the cells in the glucose synthesis/gluconeogenesis) which results in a less effective TCA process. The varying (and sometimes unpredicted) ratio between the amount of labeled octanoate salt that "takes" the TCA cycle path and the amount of labeled octanoate salt that "takes" alternative paths may affect the accuracy of the breath test.

According to some embodiments, the following steps are provided, independently from each other or in any combination, for increasing the diagnostic accuracy of the octanoate breath test:

a. Using low dosage (such as in the range of 100 mg) of octanoate salt to avoid saturation of the TCA cycle.

b. Patients may be tested after >8 hours fasting that assure that the metabolic conditions are more or less stable and less sensitive to variations which are due to consuming a meal.

c. The test meal may include glucose and $^{13}C$ octanoate salt.

d. The test meal may include aspartame (and $^{13}C$ octanoate salt), which provides aspartic acid, which is the source of oxalacetic acid.

e. An alternative to b and/or c wherein glucose/aspartame are administered prior to the test.

f. Using of drugs that block/reduce the ketonic generation path-way. (for example, HMG-CoA reductase inhibitors)

g. Measuring ketone bodies generation with biochemical tests (ketonuria and/or plasma serum ketone bodies concentration) in conjunction to the 13C-octanoate salt breath test to improve diagnostic accuracy of the test.

h. Looking for traces of 13C-octanoate salt in blood.

The term "TCA cycle" refers to the citric acid cycle, also known as the tricarboxylic acid cycle or the Krebs cycle, which is a series of enzyme-catalysed chemical reactions of central importance in all living cells that use oxygen as part of cellular respiration. In eukaryotes, the citric acid cycle occurs in the matrix of the mitochondrion.

The term "AcCoA" refers to acetyl-coenzyme A, which is an important molecule in metabolism, used in many biochemical reactions. Its main use is to convey the carbon atoms within the acetyl group to the TCA cycle to be oxidized for energy production.

According to some embodiments, improving diagnostic accuracy of the test (such as, for example, in step g), may include for example: if the measured 13C by product is low but ketone bodies are very high, this may indicate that the beta-oxidation may be normal but the TCA cycle is defective. Such a situation may have an important clinical significance.

Detection on NASH Patients

In another embodiment, there is provided a method of assisting in the detection of NASH patients based on showing octanoate breath test results, which are in the range of the results observed in normal subjects. The differentiation between patients having NASH and those who are normal is based on the presentation of the patient having clinical signs that he is suffering from the metabolic syndrome and/or optionally having abnormal liver enzymes (such as elevated ALT)), which would indicate that the patient suffers from NASH. Thereby, in a group of patients suffering from the metabolic syndrome and/or optionally having abnormal liver enzymes, (and/or optionally, in certain cases, having normal enzymes), values of octanoate breath test/beta oxidation in the range observed in normal subjects would indicate an advanced stage of the disease than in those with elevated octanoate breath test (which would be detected in patients with fatty liver with minimal or no cell injury) and may aid in classification of NASH. Ultrasound and/or CT and/or MRI might be used as an additional aid to differentiate between normal and NASH.

In another embodiment, there is provided a method of assisting in the differentiation of NASH, steatosis (NAFL) and normal based on showing octanoate breath test results combined with demographic and clinical data of the patient to generate a prediction score. In one of the preferred embodiments the score is derived from multivariate analysis.

In another embodiment, there is provided a method of assisting in the differentiation of NASH, steatosis (NAFL) and normal based on showing octanoate breath test results combined with demographic and clinical data of the patient to generate a prediction score. In one of the preferred embodiments the score to predict the condition in the target population is derived using Logistic Regression.

Challenging the Liver

The liver is an organ that has a very high metabolic capacity reserve. It is well known that a small part of a standard liver mass is sufficient to accomplish its physiological tasks. Ideally, the physician would like to get a quantitative evaluation of the liver mass, percentage of the cells that are functioning normally, or any other related parameters.

According to some embodiments, a breath test method is provided for evaluating liver function, the method may include monitoring a metabolic product of methacetin, after administering to the subject, an isotopically labeled substrate and an activation test that may challenge the liver in a way that the "essentially all" liver has to function to a normal extent to metabolize the activation test.

In another embodiment the term "activation" may refer to the use of any substance(s) that induces liver activity, for example, but not limited to, sugar, alcohol and other substances.

According to some embodiments, a breath test method is provided for evaluating liver function, the method may include monitoring a metabolic product of substrate, after administering to the subject, a dose of over the minimum amount of substrate required for evaluating liver function, where the dose may challenge the liver in a way that the "essentially all" liver has to function to a normal extent to metabolize the activation test. In another embodiment, substrate may comprise of isotopically labeled substrate. In another embodiment, substrate may comprise of isotopically labeled substrate and non-isotopically labeled substrate. In another embodiment, the dose may be higher than 75 mg. In another embodiment, the dose may be higher than 85 mg. In another embodiment, the dose may be 75-100 mg. In another embodiment, the dose may be higher than 100 mg.

In one embodiment, the term "monitoring" may refer to conducting a multiplicity of measurements. In another embodiment, conducting a multiplicity of measurements may be performed to obtain the metabolism rate of a certain substrate.

In one embodiment, the term "essentially all" may refer to a larger percent of liver cells that could be evaluated after administering the substrate alone without the activation.

In another embodiment, the term "challenge" may refer to induce the activity of a larger amount of liver cells than would be induced without the activation. In another embodiment, the term "challenge" may refer to induce the activity of a larger amount of liver cells than would be induced given the minimum amount of isotopically labeled substrate required for evaluating liver function.

In another embodiment, the term "substrate" may refer to any material that undergoes metabolism in the liver. In another embodiment, the term "substrate" may refer to methacetin. In another embodiment, the term "substrate" may refer to a combination of materials, for example, but not limited to, methacetin and octanoic acid, salt, ester or derivative thereof.

In one embodiment, a method is provided for the assessment of beta-oxidation/mitochondrial function together with microsomal function on the same day or on separate days, wherein first substrate is administered and when its metabolic rate is evaluated, the second substrate is administered. This enables one to evaluate how different liver diseases and/or metabolic conditions and/or fat impact the beta-oxidation/mitochondrial function of hepatic (liver) cells and to evaluate how these cells perform their physiological task. The "On-line" continuous analysis may enable the performance of these procedures. A non-limiting example of administering one substrate after the other is disclosed in US2005020931.

In one embodiment, two substrates (or more) are labeled with different isotopes so that they may be evaluated in parallel (for example labeling $^{13}C$ and $^{14}C$).

In one embodiment, two substrates (or more), wherein at least one substrate may be measured by a breath test and the other by other means such as, but not limited to, a dye measured optically through the skin (for example, the indocyanine green test)

In one embodiment, two substrates (or more) labeled with the same isotopes may be measured by breath test so that their average metabolism may be evaluated.

In one embodiment, algorithms that may correct for the impact of the traces of a first substrate to metabolization of the second substrate are provided. In another embodiment, the algorithms may be based on empirical and other models. Similarly, according to other embodiments, a method is provided to correct the impact of the second substrate on metabolization of the first substrate if both substrates are administered simultaneously.

Formulations of Methacetin

To assess the maximum capacity of the liver or a particular enzyme in the liver to metabolize a compound such as 13C-methacetin and the rate of its metabolization, the total amount should be fully delivered to the liver as quickly and as completely as possible. In terms of classical enzyme kinetics, one should be at zero order kinetics and not first-order kinetics. This is the case in a healthy subject for whom the amount of substrate (13C-methacetin) is not at saturation (that is, if the more 13C-methacetin is delivered to the healthy subject, the reaction rate would still be the same) and this is the reason the 13C-methacetin should be absorbed fast. In zero order kinetics, the amount of test substance does not exceed the maximum capacity of the enzyme to metabolize it, and, therefore, the rate of product production is an accurate measurement of the maximum functionally capacity of the enzyme. There could be cases where the reaction is a first order reaction, for example, when the patient has a severe liver condition, in which case, a substrate amount, which for a healthy subject would not be at saturation, would be at saturation for the patient with the severe liver condition.

Solubility of Methacetin and Methacetin-$^{13}$C:

Since the use of a stable isotope of carbon does not alter the general physical and chemical properties, all studies with Methacetin-$^{13}$C may also apply to methacetin (unlabeled) and vice versa. According to some embodiments, the term "methacetin" may refer to an isotopically labeled methacetin. According to some embodiments, the term "isotopically labeled methacetin" may refer to $^{13}$C labeled methacetin. According to some embodiments, the term "$^{13}$C labeled methacetin" may refer to methacetin-methoxy$^{13}$C. According to some embodiments, the term "methacetin" may refer to a combination of isotopically labeled and non-labeled methacetin.

The dissolution of methacetin in water (such as tap water at room temperature) is difficult even at concentrations of 75 mg to 150 ml. Furthermore, 13C-methacetin can form microcrystals and/or granule forms that further make its dissolution difficult. Common practice is to use 75 mg in 150-200 ml of tap water used oral administration, but in most cases it is difficult to assure 100% dissolution. How much may undergo decomposition in the acid environment of the stomach or may precipitate from solution is not known with certainty and may vary considerably.

Another variable is the length of time that both the insoluble and soluble methacetin enters the small intestines where absorption begins. The absorbed compound enters portal vein blood and is delivered to the liver for metabolism. The insoluble fraction must await solution in the intestinal and pancreatic fluids that enter the lumen before absorption occurs. Thus, the phase of intestinal absorption is relatively long and delivery to the liver closer to first-order rather than zero order kinetics, which lessens the ability to distinguish low from normal enzyme levels in the liver and, therefore, loss of liver function. Also, it introduced an uncontrolled variable that affects the inter- and intra-patient variability (crucial in any case also when patients are in more advanced stages of disease). The correct dosage form may improve absorption.

In the prior art, dissolving methacetin in a cap of hot tea was proposed, to facilitate dissolution. Teas, however, introduce other variables related to the effects of tea material on the test. For example, tea (or one or more materials in the tea) may affect the absorption kinetics and, most importantly, affect the hepatic metabolization.

In addition, different teas have different pH values, typically ranging between 2 and 7. The pH of teas is also dependent on tempetature. Moreover, the Methacetin ring, due to its substituted groups (methoxy and acetanidine), is active for nucleophilic reactions, such as SN1 and SN2. Due to thermodynamic considerations, the high tea temperature of the tea preparation can modify the chemical composition of the 13C-methacetin ring.

It is also known that tap water contains certain ions, such as fluorine, phosphate and chlorine ions. These ions present in tap water influence the results of enzymatic activity tests, for example, due to their reacting with the methacetin ring.

These, of course, are undesired, particularly while assessing enzymatic activity of the liver.

In one embodiment, there is provided a storage stable methacetin composition for use in a breath test, the composition comprising methacetin or a salt or derivative thereof substantially dissolved in water, wherein the composition is substantially free of methacetin products (such as anisidine).

In one embodiment, there is provided a water-soluble form of methacetin, a salt or a derivative thereof. In another embodiment, the water-soluble form of methacetin may facilitate absorption of methacetin in comparison to non-treated methacetin. In another embodiment, the absorption of methacetin may be active or passive. In another embodiment, there is provided a water-soluble form of methacetin, a salt or a derivative thereof, adapted to be fully delivered to the liver. In another embodiment, there is provided a water-soluble form of methacetin, a salt or a derivative thereof, adapted to be fully delivered to the liver at a period of time shorter than the period of time needed for delivering into the liver non-treated methacetin. In another embodiment, the term "fully" refers to 70-100%. In another embodiment, the term "fully" refers to 80-100%. In another embodiment, the term "fully" refers to 90-100%.

The term "form of methacetin" may be, according to some embodiments, a composition, complex, mixture, combination, compound, formulation, inclusion complex, and the like, that includes methacetin.

The term "water-soluble form of methacetin" may include, according to some embodiments, a form of methacetin having larger water solubility than methacetin alone.

In another embodiment, the water-soluble form of methacetin may include methacetin in combination with carrier molecule(s).

In another embodiment, the water-soluble form of methacetin may include a complex of methacetin. In another embodiment, the water-soluble form of methacetin may include an inclusion complex.

The term "complex of methacetin", according to some embodiments, may refer to methacetin reversibly associated with a complexing agent via non-covalent chemical bonds.

The term "complex of methacetin", according to another embodiment, may refer to methacetin, a salt or a derivative thereof, that may be included inside the three-dimensional net of a complexing agent.

The term "inclusion complex of methacetin", according to some embodiments, may refer to methacetin, a salt or a derivative thereof, that may be included in the inner cavity of the complexing agent.

The term "complexing agent", according to some embodiments, may refer to a substance that is reversibly associated with methacetin (for example, but not limited to, polymers, cyclodextrins and the like).

In one embodiment, the water-soluble form of methacetin may be able to achieve a substantially (over 70% (w/v)) concentration in water. In one embodiment, the water-soluble form of methacetin may be able to achieve a substantially over 80%-90% (w/v) concentration in water. In one embodiment, the water-soluble form of methacetin may be able to achieve a substantial (over 90% (w/v)) concentration in water.

In one embodiment, the water-soluble form of methacetin may be able to achieve over 99% (w/v) concentration in water.

In one embodiment, the molar ratio of methacetin and the complexing agent may be 1 to between 1 and 3. In another embodiment, the molar ratio of methacetin and the complexing agent may be 1 to between 1 and 2. In another embodiment, the molar ratio of methacetin and the complexing agent may be 1 to approximately 1.5.

In another embodiment, the molar ratio of methacetin and hydroxypropyl-beta-cyclodextrin may be 1 to 1. In another embodiment, the molar ratio of methacetin and hydroxypropyl-beta-cyclodextrin may be 1 to 1.7. In another embodiment, the molar ratio of methacetin and hydroxypropyl-beta-cyclodextrin may be 1 to between 1 and 3. In another embodiment, the molar ratio of methacetin and hydroxypropyl-beta-cyclodextrin may be 1 to between 1 and 2. In another embodiment, the molar ratio of methacetin and hydroxypropyl-beta-cyclodextrin may be 1 to between 1.5 and 2.

In another embodiment, the complexing agent may include unsubstituted or substituted cyclodextrin. In another embodiment, the cyclodextrin may include beta-cyclodextrin.

In another embodiment, the substituted cyclodextrin may include alkylated, hydroxyalkylated cyclodextrin or a combination thereof. In another embodiment, the hydroxyalkylated cyclodextrin may include hydroxypropyl-beta-cyclodextrin, hydroxyethyl-beta-cyclodextrin methyl-beta-cyclodextrin, glucose-beta-cyclodextrin, or the like, or any combination thereof. In another embodiment, the hydroxyalkylated cyclodextrin may include hydroxypropyl-beta-cyclodextrin. In another embodiment, the beta-cyclodextrin may include 2-hydroxypropyl-beta-cyclodextrin.

Cyclodextrins are cyclic oligosaccharides consisting of 6, 7, or 8 glucopyranose units, usually referred to as alpha, beta or gamma cyclodextrins, respectively. These naturally occurring compounds have relatively rigid doughnut-shaped structures, and may be used as natural complexing agents. The unique structures of these compounds owe their stability to intramolecular hydrogen bonding between the $C_2$- and $C_3$-hydroxyl groups of neighboring glucopyranose units. The molecule takes on the shape of a torus with the $C_2$- and $C_3$-hydroxyls located around the larger opening and the more reactive $C_6$-hydroxyl aligned around the smaller opening. The arrangement of $C_6$-hydroxyls opposite the hydrogen bonded $C_2$- and $C_3$-hydroxyls forces the oxygen bonds into close proximity within the cavity, leading to an electron rich, hydrophobic interior. The size of this hydrophobic cavity is a function of the number of glucopyranose units forming the cyclodextrin. The solubility of natural cyclodextrins is very poor, and initially this prevented cyclodextrins from becoming effective complexing agents. Chemical substitutions at the 2, 3, and 6 hydroxyl sites would greatly increase solubility. The degree of chemical substitution, as well as the nature of the groups used for substitution, determines the final maximum concentration of cyclodextrin in an aqueous medium. Cavity size is a major determinant as to which cyclodextrin is used in complexation. "Fit" is critical to achieving good incorporation of cyclodextrins. Six-glucopyranose unit compounds or alpha-cyclodextrins have small cavities, which are not capable of accepting many molecules. Eight-glucopyranose unit compounds or gama-cyclodextrins may, in some cases, have larger cavities than some molecules to be incorporated, and cyclodextrin hydrophobic charges cannot effectively interact to facilitate complexation. Hydrophobic molecules may be incorporated into the cavity of cyclodextrins by displacing water. This reaction may be favored by the repulsion of the molecule by water. This effectively encapsulates the molecule of interest within the cyclodextrin, rendering the molecule water-soluble. When the water-soluble complex is diluted in a much larger volume of aqueous solvent, the process may be reversed, thereby releasing the molecule of interest into the solution (The Source. (1991). Water-Soluble Complexes, Part 1: Cyclodextrins-What are they? Vol. 7 No. 3. incorporated herein by reference).

According to some embodiments, 75 mg of methacetin may be solubilized in 5 ml of 10-60% cyclodextrin in water. In another embodiment, 15 mg of methacetin may be solubilized in 75 ml of 10-50% cyclodextrin in water. In another embodiment, 15 mg of methacetin may be solubilized in 75 ml of 20-50% cyclodextrin in water. In another embodiment, 15 mg of methacetin may be solubilized in 75 ml of 30-50% cyclodextrin in water. In another embodiment, 15 mg of methacetin may be solubilized in 75 ml of 35-45% cyclodextrin in water. In another embodiment, 75 mg of methacetin may be solubilized in 5 ml of approximately 45% cyclodextrin in water.

According to some embodiments, the molar ratio between methacetin and cyclodextrin may be 1 to between 1-3. In another embodiment, the molar ratio between methacetin and cyclodextrin may be to between 1-2. In another embodiment, the molar ratio between methacetin and cyclodextrin may be 1 to approximately 1.5.

According to some embodiments, the complexing agent as referred to herein may include a polymer. In another embodiment, the polymer may include polyvinylpyrrolidone, hydroxyalkylcellulose, polyethylene glycol, sodium lauryl sulfate, Tween-80, any derivative thereof, or any combination thereof.

According to some embodiments, the ratio between methacetin and the polymer may not be critical and may depend on the desired final dose of methacetin. According to some embodiments, the complexes may include from 10% to 50% by weight of methacetin according to the total weight of the complex. According to other embodiments, the complexes may include from 10% to 20% by weight of methacetin according to the total weight of the complex. According to other embodiments, the complexes may include from 15% to 25% by weight of methacetin according to the total weight of the complex. According to other embodiments, the complexes may include from 20% to 30% by weight of methacetin according to the total weight of the complex. According to other embodiments, the complexes may include from 30% to 40% by weight of methacetin according to the total weight of the complex.

According to some embodiments, the water-soluble form of methacetin may include an organic solvent. In another embodiment, the organic solvent may be a non-toxic organic solvent. In another embodiment, the water-soluble form of methacetin may include methacetin pre-dissolved in an organic solvent.

According to some embodiments, the water-soluble form of methacetin may be in the form of a dry solid, particulates, powder, particles, and the like. In another embodiment, water may be added prior to administration.

Stability of Methacetin and Methacetin-$^{13}C$:

According to some embodiments, the water-soluble forms of methacetin, as described herein, may stabilize the methacetin and may prevent the loss of the methoxy group or other evidence of decomposition.

According to some embodiments, methacetin-$^{13}$C may be stable in water and does not undergo loss of the methoxy group or other evidence of decomposition.

Although cyclodextrins as a class of compounds are known to be useful for the solublization of other chemicals, the solubility of methacetin in hydroxypropyl beta cyclodextrin is not predictable, and other cyctodextrins such as alpha and gamma cyciodextrin, also known for their general solubilization properties, were found less effective in solubilizing methacetin.

Unexpected results showing potential enhancement of stability of the molecule, may be attributable, according to some embodiments, to the structure of methacetin, which makes it susceptible to oxidation.

In another embodiment, the disclosure also relates to pharmaceutical compositions, which may include a predetermined amount of water-soluble form of methacetin, a salt or a derivative thereof, together with one or more pharmaceutically acceptable carriers or excipients.

In another embodiment, the pharmaceutical composition may be in any form, including but not limited to a liquid, solution, gel, solid, particulates, powder, particles, and the like.

Pharmaceutically acceptable excipients may include water, binders, diluents, disintegrating agents, stabilizing agents, preservatives, lubricants, fragrances, flavoring agents, sweeteners and other excipients known in the field of the pharmaceutical technology. Carriers and excipients may include hydroxypropylcellulose, lactose, microcrystalline cellulose, calcium carbonate, starch, colloidal silicone dioxide, sodium starch glycolate, talc, magnesium stearate, polyvinylpyrolidone, and other excipients known in the field of the pharmaceutical technology.

Optionally, according to some embodiments, the pharmaceutical compositions may be combination products including one or more active components in addition to methacetin.

Pharmaceutical compositions in a solid dosage forms, may be, in accordance with some embodiments, tablets with immediate release of the methacetin, effervescent tablets or dispersion tablets and capsules.

The pharmaceutical compositions may be prepared by methods known in the field of the pharmaceutical technology.

In contrast to the current form of administration, specifically, methacetin in water, it is possible, according to some embodiments, to deliver all the pre-determined amount of methacetin as a small bolus that quickly clears the esophagus and enters the stomach, where some dilution by gastric juice can occur. In another embodiment, dilution of the bolus does not cause precipitation of the methacetin, and it will all be delivered more quickly to the intestines for absorption.

In one embodiment, because a complexing agent, for example hydroxypropyl beta cyclodextrin, maintains the solubility of methacetin, a greater concentration may come in contact with the intestinal mucosa, and more rapid absorption ensues.

Thus, the administration of a water-soluble form of methacetin more closely approaches zero order kinetics and may be a more uniform test for functional liver capacity.

In one embodiment, there is further provided a method for the preparation of a water-soluble form of methacetin, a salt or a derivative thereof, the method may include dissolving a complexing agent in water and adding methacetin, a salt or a derivative thereof. In another embodiment, the method further includes stirring the mixture at a temperature in the range from about 20° C. to 100° C. (for example, but not limited to, stirring the mixture at a temperature in the range from about 20° C. to 30° C., until the methacetin, a salt or a derivative thereof are inserted and dissolved into the complex). In another embodiment, a complexing agent is used and or inserted into the complex at temperatures in the range of 20-100° C.

In another embodiment, the method further includes drying in any appropriate manner, for example, but not limited to, lyophilization, spray-drying, fluid bed dryer, static oven, and any other suitable method.

In another embodiment, the method further includes encapsulating the water-soluble form of methacetin. According to some embodiments, the capsule (which may be fast, slow or controlled release) may be swallowed and dissolves in gastric juice in the stomach and may quickly enter the intestines as a small bolus. In another version, the capsule may be enteric-coated and may not be dissolved until after entering the intestines. Dissolution of the capsule delivers the methacetin immediately and in large concentration to the absorbing surface, thus yielding high concentrations in the portal vein, which delivers the medication to the liver.

In another embodiment, the disclosure relates to use of the water-soluble form of methacetin, a salt or a derivative thereof, for the preparation of a pharmaceutical composition for use in testing liver functional capacity.

In accordance with some embodiments, the water-soluble form of methacetin may be used in any of the methods referred to herein. In another embodiment, the water-soluble form of methacetin may be used in any test that evaluates the liver function. In another embodiment, the water-soluble form of methacetin may be used in any breath test that evaluates the liver function. According to some exemplary embodiments, the water-soluble form of methacetin may be used in any method that would be known to one of skill in the art for testing a liver function, for example, as disclosed in the following publications: B. Braden, d. Faust, u. Sarrazin, s. Zeuzem, c. F. Dietrich, w. F. Caspary & c. Sarrazin, *$^{13}$C-methacetin breath test as liver function test in patients with chronic hepatitis C virus infection*, Aliment Pharmacol Ther 2005; 21: 179-185 and Klatt S, Taut C, Mayer D, et al. *Evaluation of the $^{13}$C-methacetin breath test for quantitative liver function testing*, Z Gastroenterol 1997; 35: 609-14, which are herein incorporated by reference.

EXAMPLES

Methacetin Solutions—Two Weeks/Three Month Stability Results

1. Tested Materials 1-1. Methacetin, PPG-400 and tween-80, were supplied by sponsor.

1-2. Sodium lauryl sulfate-(SLS): Analytical grade for HPLC.

1-3. Water: HPLC grade after 0.2μ filter.

1-4. Acetonitrile: HPLC grade.

1-5. Methanol: HPLC grade.

1-6. Methacetin in sterile water.

2. Formulations Preparation

In the first three items, formulations containing 75 mg methacetin/200 mL solvent were prepared:

2-1. Formulation-1: 76.04 mg methacetin; 62.94 mg SLS; water to final volume of 200 mL.

2-2. Formulation-2: 75.87 mg methacetin; 4 mL PPG-400; water to final volume of 200 mL.
2-3. Formulation-3: 76.66 mg methacetin; 4 mL tween-80; water to final volume of 200 mL.
In the fourth formulation, 75 mg methacetin/100 mL solvent was prepared:
2-4 Formulation-4: 75.01 mg methacetin; dissolved in 70° C. sterile water to final volume of 100 ml.
3. Storage Conditions The first three formulated solutions were stored at room temperature protected from light. The fourth solution was stored in an incubator for 3 months at 40° C.
4. Sample Preparation Before Analysis.

On each testing interval, the formulated samples were analyzed according to the following method:
Method of Analysis:

| HPLC conditions: | |
| --- | --- |
| Column: | Inertsil ODS-2, 5μ. 250 × 4.6 mm, |
| Column temp: | 30° C. |
| Detector: | UV at 240 nm |
| Flow: | 0.9 mL/min |
| Injection volume: | 15 μL |
| Run time: | 9 min |
| Mobile phase: | 30:70 ACN:$H_2O$ |
| Blank: | M.P. |

The samples were diluted to a concentration of about 37 ppm (37 mg in 1000 ml) and analyzed against a standard solution at the same concentration. The standard was provided by the sponsor (Adrich 428264 batch: UI 2335). Purity of 100% was used in calculations.
5. Methacetin Standard Solution Preparation.

The methacetin sample that was used for the formulations was also used as a standard for the HPLC determination.

Stock solutions containing 37-38 mg/100 mL methanol were found to be stable at room temperature for at least one week. The stock solution was diluted ×10 in mobile phase solution before the HPLC analysis.
6. Assay of Methacetin in the Formulations The assay was conducted according to Analyst SOP No. 05-001-03, and the HPLC method that was provided by the sponsor.
7. Results The results as given in Table 1, show that, in the first three formulations, methacetin was found stable at room temperature for two weeks, and the fourth formulation was found to be stable for 3 months.

Reproducibility and Stability of Single Dose Preparation of Methacetin in Sterile Water.

Table 2 shows the reproducibility and stability of sample preparation $^{13}C$ Methacetin, 75 mg/100 ml (Analyst Research Laboratories)

TABLE 2

Reproducibility and Stability of $^{13}C$ Methacetin

| Analyst # | mg/mL | Sample volume (mL) | Mg/bottle |
| --- | --- | --- | --- |
| Reproducibility | | | |
| 9644-1 | 0.79 | 95.0 | 75.3 |
| 9644-2 | 0.77 | 98.0 | 75.4 |
| 9644-3 | 0.77 | 97.0 | 74.2 |
| 9644-4 | 0.75 | 98.5 | 73.9 |
| 9644-5 | 0.77 | 97.5 | 75.2 |
| 9644-6 | 0.76 | 96.5 | 73.3 |
| 9644-7 | 0.77 | 97.0 | 74.5 |
| 9644-8 | 0.76 | 99.5 | 75.6 |
| 9644-9 | 0.76 | 98.0 | 74.1 |
| 9644-10 | 0.76 | 100.5 | 76.3 |
| Mean | 0.77 | 97.8 | 74.8 |
| % RSD | 1.5 | 1.6 | 1.2 |
| Stability (3 months at 40° C.) | | | |
| 9644-1 | 0.79 | 95.0 | 74.2 |
| 9644-2 | 0.77 | 98.0 | 74.1 |
| Mean | | | 74.2 |

Stability of Methacetin in Cyclodextrin
1. Formulation Preparation

Formulation containing 175 mg methacetin in 5 ml Cyclodextrin was prepared.
2. Methacetin Standard Solution Preparation.

Aqueous solutions of Methacetin were prepared in the laboratory at concentrations of ~500 ppm in 4 replicates. Methacetin content was determined by Reverse Phase UV Detection HPLC method at the day of preparation. The samples were stored at room temperature for the required time period of the analysis and were analyzed against prepared standard solutions.
3. Results The results as given in Table 3, show that methacetin in the new formulation was found to be stable at room temperature for five weeks.

TABLE 1

Stability results - summary

| Formulation no. | Time zero | | One week | | Two weeks | | Max. % difference from time zero |
| --- | --- | --- | --- | --- | --- | --- | --- |
| | Assay (μg/mL) | Appearance | Assay (μg/mL) | Appearance | Assay (μg/mL) | Appearance | |
| For 1 | 383.0 | Clear, no | 380.9 | Clear, no | 383.6 | Clear, no | |
| (SLS) | 382.9 | color, no | 381.2 | color, no | 383.5 | color, no | 0.5 |
| Mean | 382.9 | precipitation | 381.0 | precipitation | 383.6 | precipitation | |
| For 2 | 371.1 | turbid, no | 369.1 | turbid, no | 370.8 | turbid, no | |
| (PPG) | 370.9 | color, no | 369.5 | color, no | 370.3 | color, no | 0.5 |
| Mean | 371.0 | precipitation | 369.3 | precipitation | 370.5 | precipitation | |
| For 3 | 372.7 | Clear, no | 371.1 | Clear, no | 376.6 | Clear, no | |
| (TWEEN) | 372.1 | color, no | 371.2 | color, no | 375.5 | color, no | 1 |
| Mean | 372.4 | precipitation | 371.1 | precipitation | 376.1 | precipitation | |

TABLE 3

Five weeks stability results - summary

| Formulation Methacetin and Cyclodextrin | TIME ZERO | | THREE WEEKS | | FIVE WEEKS | | Max. % difference from time zero |
|---|---|---|---|---|---|---|---|
| | Assay (mg/5 mL) | Appearance | Assay (mg/5 mL) | Appearance | Assay (mg/5 mL) | Appearance | |
| | 175.0 | Clear, no | 175.0 | Clear, no | 168.75 | Clear, no | 3.6 |
| | 175.0 | color, no | 177.7 | color, no | 178.0 | color, no | |
| Mean | 175.0 | precipitation | 176.35 | precipitation | 173.375 | precipitation | |

"Physiological Noise" for Evaluation of Severity of "Hepatic Impairment"

Another preferred embodiment of the present invention suggests adding a new parameter derived from the magnitude and/or level of the physiological fluctuations (may also be referred to as physiological noise) in the liver dynamic function response/curve.

It was, surprisingly, found that while in normal subjects or in patients with moderate liver damage the $^{13}$C-Methacetin Breath Test PDR (Percentage Dose Recovery) Curve observed is relatively smooth, in patients with advanced diseases (for example, in patients with advanced cirrhosis categorized as being Child-Pugh class B or C) the curve may include noise which represents an overall disturbed "hepatic function" or "hepatic impairment". It is important to mention that the overall hepatic function depends on both the blood flow into the hepatic cells and the metabolization within the cells and elimination of by products.

While in patients with advanced disease, the level of metabolization can remain high (graph's height) due to induction of P450 activity by different processes, and thereby be within the normal values, a significant disease can be detected by appearance of noise in these patients.

Figure 4:
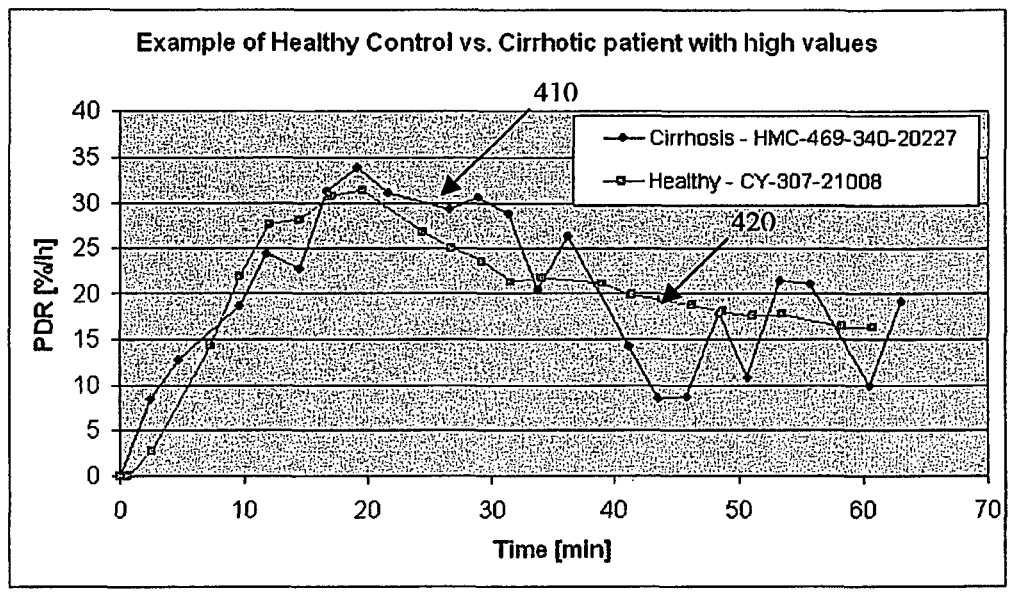
FIG. 4 shows two $^{13}$C-Methacetin Breath Test PDR (Percentage Dose Recovery) Curves, according to some embodiments.

The following are two examples that illustrate this phenomenon. Reference is now made to FIG. 4, which shows two $^{13}$C-Methacetin Breath Test PDR (Percentage Dose Recovery) Curves: curve 410, which represents cirrhotic patients with normal (high) values, and curve 420, which represents a healthy control group. Although the maximum heights of both curves (curve 410 and curve 420) are similar, curve 420 is relatively smooth, while curve 410 shows noticeable fluctuations.

The wealth of information derived from the methacetin breath test, which monitors not only the magnitude of metabolization, metabolization rate PDR, accumulated metabolization, CPDR, but also the dynamic response: for example, PDR peak time and height and the "physiological noise" can allow to also evaluate portal hypertension/HVPG (hepatic venous pressure gradient) and number of shunts as the breath test is affected by these factors and not just by the hepatic cell metabolic processes.

It has been shown by recent studies that HVPG (hepatic venous pressure gradient) provides a reliable prognosis score in patients with liver diseases. The problems with HVPG tests are that they are invasive and expensive.

It is well known that as a liver disease progresses, changes in tissue and blood vessel occur. In particular, this includes generation of shunts. Recent studies have shown that shunt tests can be highly valuable as a prognosis score (more information can be found in Everson G T, Shiffman M L, et al, Aliment Pharmacol Ther. 2008 May; 27(9):798-809 incorporated by reference in their entirety).

Another preferred embodiment of the present invention is to utilize the methacetin breath test to evaluate HVPG/portal hypertension and shunting. The reasoning is that methacetin is a drug with a high hepatic extraction ratio (as known in the art, for example, more than 0.8) and, for this reason, is also dependent on the blood flow to the liver. The association of histological changes in the liver and haemodynamic changes and portal hypertension in cirrhotic patients has been recently presented [Kumar M. et al, Aliment Pharmacol Ther. 2008 May; 27(9):771-9, which is incorporated herein by reference in its entirety]. The sensitivity of methacetin to shunts has been recently presented at AASLD 2007, by the Prof. A. Gasbarrini group (from the Catholic Univ., Rome, Italy).

The term "Physiological noise" as referred to herein may be defined, according to some embodiments, as the magnitude, amplitude, frequency and/or number of fluctuations in a curve, such as a breath test curve, for example, a percentage dose recovery (PDR) curve and/or a delta over baseline (DOB) curve of an isotope labeled methacetin, a salt or a derivative thereof or any other appropriate chemical substance.

Hepatic Impairment Score

A preferred embodiment of the present invention provides a new score termed "Hepatic Impairment Score", and an algorithm for computing same, used to quantitatively and qualitatively assess the severity of hepatic impairment/diseases severity in individuals. This can be used for example for:

(i) first/preliminary evaluation of disease severity—such as detection of cirrhosis, significant fibrosis and/or significant inflammation, evaluation of liver reserve;

(ii) follow up individuals and serve as an "end-point" or "surrogate marker" to assess changes in patient's condition over time and monitor therapy in particular;

(iii) provide prognosis information and/or predict at least one of the following:

Mortality;

Any complication including: bleeding varices, encephalopathy, synthetic function deterioration, high bilirubin;

Portal hypertension;

Need for liver transplantation; and/or

SBP (spontaneous bacterial peritonitis);

According to some embodiments, it is an objective of the present invention to provide a reliable score, which includes, in addition to data derived directly from the breath test, demographic information on the patient. The demographic information can be used to:

(i) compensate for inter-patient factors that affect a breath test; and/or (ii) deal with factors that affect disease and that, together with breath test data, can allow provision of a reliable predication of disease severity and/or status. The information may relate to any one or more items from the following list (and/or to any other relevant information):

Height and weight;

Age;

Gender;

Smoking habits;

Disease etiology;

Known information about complications such as, but not limited to, shunts, portal hypertension, encephalopathy, abnoram blood test such as bilirubin, edema and/or ascites, decompensated cirrhosis, consumption of certain drugs that may impact the metabolic path of methacetin; and Common scores that assess liver disease severity such as the Child-Turcotte-Pugh (CTP) or MELD scores.

A non-limiting example of utility of clinical information in the algorithm can be using an algorithm wherein the "physiological noise" parameter contributes to the "hepatic impairment score" only when it's known that the user suffers from "decompensated cirrhosis" and not otherwise, as it may degrade performances in patients with less sever liver disease. Using logistic regression techniques, it was surprisingly found that the physiological noise has a negative effect on performances with asymptomatic patients only while it is contributing in more advanced liver disease and wherein a group that includes a wide range of severity from normal to end-stage disease is evaluated.

Score structure—according to exemplary embodiments, the score may be structured as a probability score, and provide values from 0 to 1 for probability of condition (derived from logistic regression for detection of a specific condition; in other words, dichotomous classification of patients) or as general score such as a liner combination of a set of parameters. The score may be structured by any other appropriate bio-statistical, mathematical method and/or any other method.

According to some embodiments, it is an objective of the present disclosure, to provide a reliable score, which includes, in addition to data derived directly from a standard breath test, parameters which include information derived from one at least of the following:

"Physiological noise";

Appearance of an early peak—the early position of the peak which is affected both by the metabolization within the hepatic cells and the blood flow and can be taken into account as a factor in algorithm and/or criteria of for which algorithm to use; and Value of parameter vs. those expected in normal—The algorithm can be constructed as an expert decision system wherein the contribution of specific parameter depends on its value. Thus, if the value of a specific parameter strongly indicates that the function is normal or that there is a significant disease (for example, liver impairment), its contribution in the algorithm will be higher than of another parameter with a borderline value.

Figure 5:
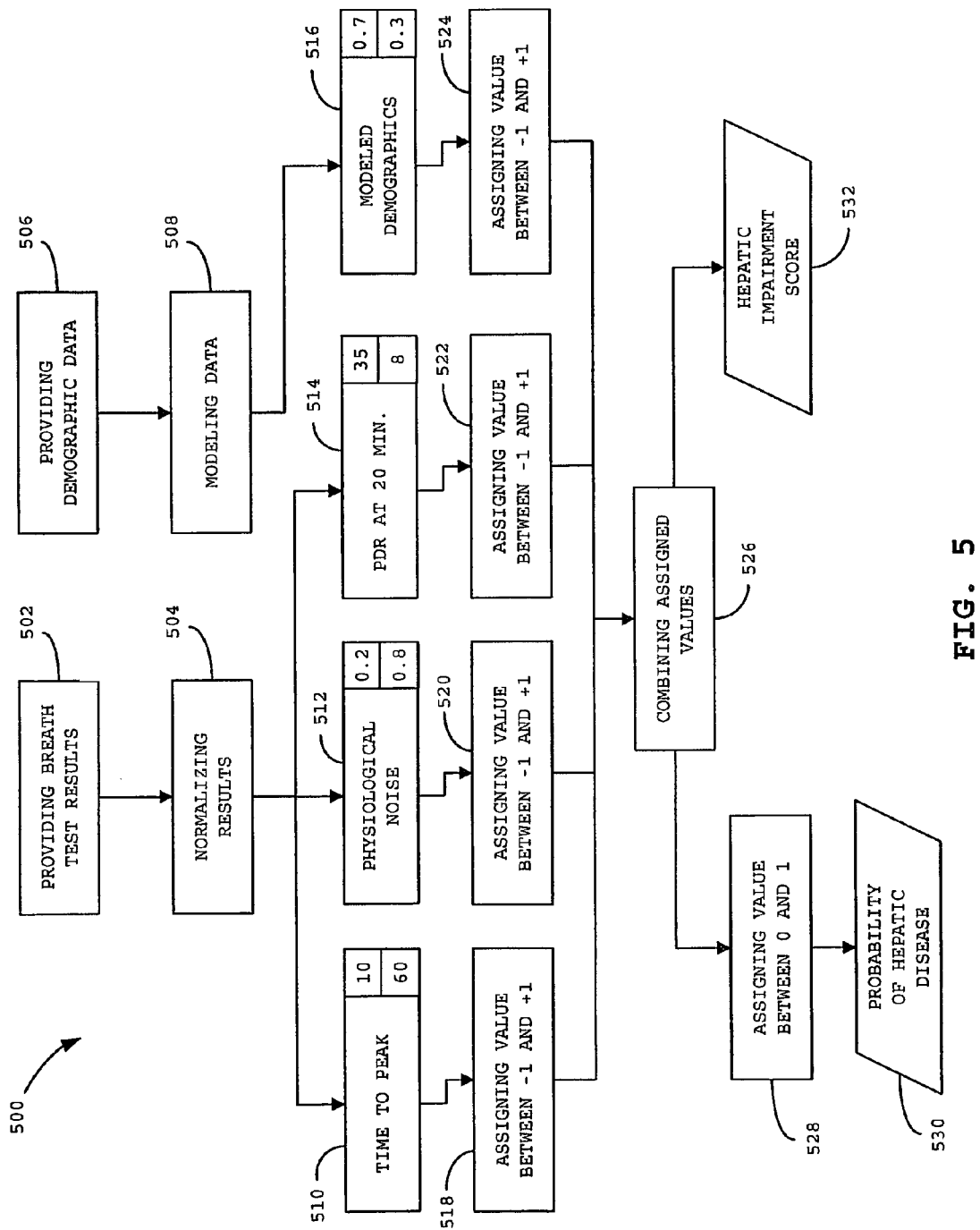
FIG. 5 shows an example of an algorithm used to detect significant fibrosis in Viral hepatitis C(HCV) patients, according to some embodiments.

Reference is now made to FIG. 5, which shows a flowchart of an exemplary algorithm 500 for detecting a liver condition, for example, used to detect cirrhosis in patients with chronic liver disease and/or assess disease severity. Algorithm 500 may optionally be implemented as an expert system.

In block 502, results of a breath test are provided. The results may include one or more parameters such as time to peak, physiological noise, PDR (Percentage Dose Recovery) at a certain time, such as 20 minutes, and/or any other parameter. In block 504, one or more of the results is optionally normalized, according to demographic data such as age and/ or to conform it to a numerical range suitable for algorithm 500.

In block 506, demographic data is provided. The demographic data may include one or more parameters such as the patient's age, gender, medical history and/or the like. In block 508, one or more parameters of the demographic data are optionally modeled, to create a numerical index reflecting the patient's proneness to hepatic conditions, based on his or her demographic data.

Blocks 510-516 show exemplary parameters related to breath test results and demographic data. Each parameter is optionally assigned two numerical thresholds: an upper threshold and a lower threshold, wherein a value exceeding the upper threshold indicates that the parameter is clinically normal, a value exceeding the lower threshold indicates that the parameter is clinically problematic, and a value between the two thresholds is considered insignificant. The upper threshold is shown in the figure inside a box lying above a box with the lower threshold.

Threshold shown in the figure are meant for illustrative purposes only. Other one or more thresholds may apply.

The upper threshold is not necessarily of a higher numerical value than the lower threshold. Some parameters, such as those of blocks 510 and 512, may include an upper threshold, which is numerically lower than a lower threshold. That is, such parameters are considered clinically problematic when they are of a higher value, and clinically normal when of a lower value.

Block 510, which stems from the breath test results, shows a "time to peak" parameter, having an upper threshold of 10 minutes and a lower threshold of 60 minutes.

Block 512, which stems from the breath test results, shows a "physiological noise" parameter, having an upper threshold of 0.2 and a lower threshold of 0.8.

Block 514, which stems from the breath test results, shows a "PDR at 20 minutes" parameter, having an upper threshold of 35 and a lower threshold of 8.

Block 516, which stems from the demographic data and breath test data, shows a "modeled demographics and breath test" parameter, having an upper threshold of 0.7 and a lower threshold of 0.3. This model can be derived using logistic or linear regression, for example, to correlate with a reference standard (such as a biopsy).

In blocks 518-524, a value between −1 and +1 is assigned to each of the parameters of blocks 510-516, respectively. A value of 0 is assigned to parameters whose value is between this parameter's thresholds. In 520-524 a negative value, of between 0 and −1, is assigned to parameters whose value exceeds the lower threshold—meaning they are clinically problematic parameters. The exact negative value is determined according to the degree of deviation from the lower threshold. Contrarily, a positive value, of between 0 and +1, is assigned to parameters whose value exceeds the upper threshold—meaning they are clinically normal parameters. The exact positive value is determined according to the degree of deviation from the upper threshold. The closer the value is to 1 or −1 the more significant the result is; for example in 518, crossing the threshold result in +1 or −1 regardless of the distance from threshold.

In a block 526, the values assigned in blocks 518-524 are combined into a single index, using a mathematical method such as summation, multiplication, averaging, weighing, and/ or any other appropriate mathematical method.

Exemplary algorithm 500 produces two outputs. A first output is shown in block 532: a hepatic impairment score. The hepatic impairment score may be the index created in previous block 526, or a modification of this index, indicating a clinical condition of the patient's liver.

A second output is shown in a block 530: a probability of hepatic disease/condition in the patient. This probability may be produced in a previous block 528, in which the index of block 526 is conformed to a range between 0 and 1. A value of 0 indicates that the probability the current patient is affected by a hepatic disease is high, whereas a value of 1 indicates that the probability the current patient is affected by a hepatic disease is high. Moreover, the probability value may be compared to two numerical thresholds: an upper threshold and a lower threshold, wherein a probability value exceeding the upper threshold may indicate that the patient's condition is clinically normal, a value exceeding the lower threshold may indicate that the patient's condition is clinically problematic.

A Storage Stable Composition of Methacetin

According to some embodiments, there is provided a storage stable methacetin composition. The importance of providing a composition of a methacetin solution having a known and stable amount of methacetin is described herein. The freedom to select different formulations is limited by the nature of the liver breath test, as different ingredients may affect not just the bio-availability but also the actual metabolization of methacetin through undesirable effects on the liver (the patient performs the test after >8 hours fasting exactly to overcome these problems/issues).

The term "methacetin composition" or "composition of methacetin" may refer, according to some embodiments, to a formulation and or drug form that includes methacetin, for example, but not limited to, methacetin in aqueous solution. According to some embodiments, the term "methacetin composition" or "composition of methacetin" may also be interchangeably referred to as "methacetin preparation" or "preparation of methacetin". The methacetin composition may include, for example, a single dose of methacetin. The methacetin composition may include, for example, a single diagnostic dose of methacetin.

Controlled Microbial Preparation

There is provided, according to some embodiments, a controlled microbial preparation of $^{13}$C-Methacetin solution.

Since it has been shown that $^{13}$C-Methacetin solution does not inhibit microbiological growth (a "challenging test" was performed and in order to comply with the requirements expressed in the previous paragraph regarding the utilization of additives of the type of chemical preservatives, a particular process for the preparation of the formulation has been developed.

According to some embodiments, it is therefore an object of the present invention to provide a microbial controlled or aseptic preparation and filling method of methactin solution into bottles without the use of preservatives. This is based on the fact that a solution is administered orally (PO) and that limited microbial load is permitted such as Total Aerobic Microbial Count (Bacteria)<$10^3$ (for example, <$10^2$) cfu/bottle. Total Yeast and Molds (Fungi)<$10^3$ cfu/bottle (for example, <$10^2$). and the absence of *E. Coli*.

A controlled process was performed wherein microbiological bioburden (microbial limit testing) was monitored during the preparation, the solution was filtered with the utilization of a two layers-autoclaved polyethersulfone filter of 0.8 and 0.2 micron, and the filling zone of the packaging machine was masked from direct contact with the ventilation system. The utilized containers and caps were sterilized with the utilization of gamma-radiation of 2.5 Mrad and Ethylene oxide (specific process parameters to be received) as sterilizing agents.

Controlled Dissolution of Methacetin

Generally, shelf life properties of the chemical solutions, such as methacetin solution, have their limitations. It was observed that certain variation of the pH may occur during the preparation and storage of the methacetin pharmaceutical product. Additionally, it is observed that the $^{13}$C-methacetin decomposes to by-products (degradant materials) during storage at accelerated and ambient conditions. One of the main degradants is chemically defined as p-anisidine. The appearance of the degradant indicates the existence of at least three main problems:

1) The concentration of methacetin decreases during storage to an unknown extent. When the patient takes the methacetin prior to the breath test, the quantity of methacetin taken by his/her body is unknown and results of the breath test, which are based on the preliminary quantity of methacetin, are therefore not accurate or may be even wrong.

2) byproduct(s) such as anisidine (such as p-anisidine) has higher pH (more basic properties) than the $^{13}$C-methacetin itself. Therefore, even when p-anisidine appears at low concentrations, this material is capable of making modifications of the pH in gross values. Moreover, there is a possibility that the pH increases as a result of the byproduct(s), such as anisidine (such as p-anisidine) presence, which accelerates the decomposition of the $^{13}$C-methacetin for further transformation into p-anisidine.

3) some of the byproduct(s) such as anisidine (such as p-anisidine) are considered to be a toxic material, and its presence in a pharmaceutical composition is undesired.

Therefore, one of the objectives of the present invention, according to some embodiments, is to lower the degradation rate of the active material (methacetin).

It was surprisingly found that the stability of methaceting in the solution depends on the dissolution conditions. There is thus provided, according to some embodiments, a method of controlled dissolution of methacetin. Methacetin seems to be stable after short term warming to <80° C. in solution. Methacetin does not dissolve well in water at room temperature (approximately 25° C.); it has long dissolution times even when micronization or lyophilization (freeze drying) technologies are implemented. Therefore, according to an embodiment of the invention, a solution of methacetin may be prepared by dissolution in warm water. It was found that even a relatively long warming time results in a negligible decomposition of methacetin. For example, it was found that only 0.018% of methacetin decomposes after heating at 80° C. for three hours.

It was also found, however, that even though the decomposition of methacetin is negligible in the short term after heating, it becomes more significant after a period of time. In other words, after a period of time has passed from the heating, decomposition by-products are found in the methacetin solution in amounts which cannot be considered negligible anymore. Therefore, heating the methacetin solution may have a delayed effect on the decomposition of methacetin, which is of course undesired.

It was surprisingly found that when methacetin is dissolved in water at room temperature by a long mixing process, as opposed to mixing it with warm water, the appearance of methacetin's decomposition by-products such as anisidine, for example, p-anisidine, (as measured in accelerated stability tests at 40° C.) is reduced or non existing even after a long period of time. This is significant as p-anisidine may introduce safety concerns even at small doses (See also Example B hereinafter).

Controlled Packaging

It was surprisingly found that the packaging configuration is critical for the physical and chemical stability of the preparation; in other words the packaging configuration is critical in order to (i) assure long term stability; (ii) avoid both absorption/adsorption effects (for example, to the walls of the container); and (iii) avoid decomposition of methacetin and appearance of by-products.

The parameters to avoid are the pH increase and the appearance of by-products such as anisidine, for example, p-anisidine, during storage of the methactin solution.

The packaging configuration that assures long term shelf life for the preparation consists of amber thermoplastic polyester resin (PET) with a polypropylene closure system and a polyethylene liner.

In another embodiment of the present invention there is provided a methacetin solution package comprising a PET bottle.

According to some embodiments, one of the objectives of the present invention is to obtain a methacetin drug form having a reasonable shelf-life at room temperature.

According to some embodiments, there is provided herein a methacetin formulation consisting of 75 mg (milligram) of the active component, $^{13}$C-methacetin, dissolved in 150 mL (milliliter) of purified water. According to some embodiments, there is no utilization of preservatives to protect the product from microbiological contamination. According to some embodiments, there is no utilization of a buffer component that is capable of maintaining the pH, regardless of whatever chemical change occurs in the preparation or during storage of the product.

It was observed that certain variation of the pH may occur during the preparation and storage of the methacetin pharmaceutical product. Additionally, it is observed that the $^{13}$C-methacetin decomposes systematically to a single main degradant material during storage at accelerated and ambient conditions. As mentioned before, the main degradant is chemically defined as p-anisidine.

Therefore, one of the objectives of the present invention, according to some embodiments, is to lower the degradation rate of the active material (methacetin).

It was surprisingly found that large differences exist in the shelf life properties when the composition is stored either in glass or PET (thermoplastic polyester resin) bottles, and that PET seems to perform better. Therefore, all subsequent experimentation was performed in both types of containers.

In the preparation phase, although $^{13}$C-methacetin is known to be a soluble compound in aqueous media, it is hard to dissolve it and to prepare a homogeneous solution without heating the solvent in advance. According to some embodiments, the preparation of methacetin "single dose" includes mixing the methacetin in warm water and, after homogenous solution is achieved, the solution returns to room temperature and the single dose bottles are filled.

Controlled pH

It has been observed that degradation of methacetin in standard preparation (based on dissolving methacetin in warm water and storing it in glass bottles) is accompanied by a rise in pH, for example, from approximately 8 to 10. Thereby, attempts to stabilize the solution with three different buffers (pH 3.5, 4.5 and 4.5) were made. Accelerated stability tests at 40° C. indicate that this approach does not seem to stabilize the methacetin solution (even when prepared by dissolution at room temperature).

An optional mechanism in the decomposition of the 13C-methacetin is amide hydrolysis (methacetin is a secondary amide) at moderately low or moderately high pH. At these pH values the methacetin may be converted into the parental acid and amine reactants in its formation, following a type of reaction as follows:

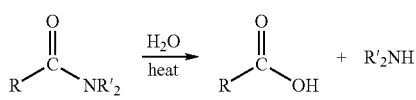

By this path the p-anisidine may be a main degradant in the decomposition of the methacetin (for example, Organic Chemistry, N. Allinger, M. Cava, D. DeJongh, C. Johnson, N Lebel and C. Stevens).

Glass containers (for example, borosilicate) release, by a bleeding mechanism, traces of sodium silicates and alkaline metal oxides (glass components) into the aqueous media. The hydrolysis of these salts generates a pH increase that may further decompose the methacetin (the amide) to its precursors. It was observed that the appearance of p-anisidine follows the increase in pH.

As described hereinbelow, low pH buffers have been demonstrated not to confer stability to the methacetin solutions.

Plastic bottles that are not capable of modifying the pH of the solution beyond certain range may maintain the methacetin solution parameters during its shelf life period.

EXAMPLES

Example A

Stability of Methacetin Single Dose in Different Containers and Buffers

Utilization of buffer solutions may fix the pH value to a certain extent regardless of whatever chemical change is occurring in the formulation. This is done by the utilization of pre-prepared buffer solutions with a defined pH and subsequently added to the preparation. A description of the buffer solutions utilized, and a summary of results during the stability program, will be represented in the following paragraphs.

Table 4, summarizes the buffer compositions utilized, the pH values obtained, the concentration of the p-anisidine in the PET and glass containers at the preparation time, as well as function of stability pull points. It is surprisingly found that fixed pH values deteriorate the further the quality of the composition. Additionally, it is observed that in purified water the pH possess high variability without a defined trend. Moreover, the pH electrode memory effect might have its influence when measuring low concentration of solute in purified water such as 0.05% concentration solutions as in the $^{13}$C-methacetin solutions.

TABLE 4

Buffer compositions, pH values, p-anisidine concentrations in PET and glass containers at different pull points in a stability program.

| sample description | | p-Anisidine (%) (left column); pH (right column) | | | | | | | | |
|---|---|---|---|---|---|---|---|---|---|---|
| Packaging | Medium | t = 0 | | 1 Week Acc., | | 2 Week Acc., | | 1 Mo Acc., | | 2 Mo Acc., |
| PET | Buff. | 0.01 | 3.52 | 0.13 | 3.48 | 0.26 | 3.51 | 0.59 | 3.54 | 1.22 | 3.55 |
| Glass | Phosphate, pH = 3.48 | 0.01 | 3.52 | 0.11 | 3.56 | 0.25 | 3.59 | 0.48 | 3.61 | 0.97 | 3.65 |
| PET | Buff. | ND | 4.50 | 0.01 | 4.47 | 0.06 | 4.50 | 0.06 | 4.48 | 0.12 | 4.49 |
| Glass | Acetate, pH = 4.49 | ND | 4.52 | 0.01 | 4.50 | 0.02 | 4.53 | 0.05 | 4.51 | 0.10 | 4.52 |
| PET | Buff. | ND | 4.60 | 0.01 | 4.54 | 0.03 | 4.58 | 0.06 | 4.57 | 0.12 | 4.54 |
| Glass | Benzoate, pH = 4.50 | ND | 4.60 | 0.01 | 4.56 | 0.02 | 4.59 | 0.05 | 4.59 | 0.10 | 4.57 |
| PET | Purified Water | ND | 5.33 | ND | 5.80 | ND | 5.10 | ND | 5.01 | ND | 5.54 |
| Glass type 3 | | ND | 6.35 | ND | 6.72 | ND | 6.82 | ND | 6.62 | 0.015 | 6.88 |
| Glass Type A | | ND | 6.15 | ND | 6.65 | ND | 6.49 | 0.04 | 7.48 | 0.04 | 7.25 |

(ND = not detected)

It can be seen from Table 4 that in purified water, particularly while the methacetin solution was maintained in a PET container, the p-anisidine concentrations are lowest over time.

According to some embodiments, the term "purified water" may refer to Purified Water (PW) as described in the USP 23 monograph as follows:

"Purified Water is water obtained by distillation, ion-exchange treatment, reverse osmosis, or other suitable process. It is prepared from water complying with the regulations of the US. Environmental Protection Agency (EPA) with respect to drinking water. It contains no added substances."

Regarding the bacteriological purity of PW, the monograph (legally enforceable section) states only that PW must comply with the EPA regulations for drinking water. The EPA regulations only specify limits for coliform bacteria. In the informational section of the USP 23, which deals with action guidelines for the microbial control of ingredient water, it says:

"A total microbial (aerobic) count that may be used for source drinking water is 500 colony-forming units (cfu) per mL. A general guideline for Purified Water may be 100 cfu/mL."

USP23 Supplement 5, effective since November 1996, specifies the method for total bacteria counts. It states:

"Heterotrophic Plate Count of a 1-mL sample, using Plate Count Agar at an incubation temperature of 30 to 35 degrees Celsius for a 48-hour period (minimum)."

Effective Nov. 15, 1996, the former inorganic chemistry tests (for calcium, sulfate, chloride, ammonia, and carbon dioxide) were replaced with a three stage conductivity test. The conductivity limit is pH dependent, but, for example, at pH 7.0, conductivity should be less than 5.8 microSiemens/cm. The former test for oxidizable substances was replaced with a Total Organic Carbon (TOC) limit of 0.05 mg/L. TOC is an indirect measure of organic molecules present in water measured as carbon. The new tests allow continuous in-line monitoring of water using instrumentation rather than lab work.

Example B

Conditions for Dissolving Methacetin

It was evaluated whether the thermal cycle for dissolving the API (active pharmaceutical ingredient, such as methacetin) can be eliminated from or at least lowered in the process. Cold vortexing, as well as the assistance of excipients acceptable by the international pharmaceutical regulations and capable of assisting in improving the dissolution of the API, were utilized. A summary of the procedures involve will be described in the paragraphs below.

Experimentation trials were performed, in order to eliminate the heating stage while dissolving the API (methacetin) in purified water. The heating and cooling stages in the preparation, when considered at commercial scale preparation, comprise a time consuming operation without efficient utilization of the production equipment.

Therefore, alternative directions for improving the API dissolution were tried. Solvents capable of dissolving the API and approvable for utilization in pharmaceutical preparations were utilized for this task.

30% by volume of the purified water of the preparation was replaced by the alternative solvent. The dissolving time of each preparation was recorded.

Table 5 represents the solvent utilized, the thermal conditions applied for the dissolution (preparation temperature) and the time needed for full dissolution of the API (methacetin) in the aqueous media.

TABLE 5

Alternative solvents, conditions and dissolving time for different preparation tracks

| Alternative Solvent | Temperature Conditions, ° C. | Dissolving Time, min |
|---|---|---|
| Purified Water | 25° C. (room temperature, RT) | 77 |
| Purified Water | 55° C. | 13 |
| Propylene Glycol 45 | 25° C. (RT) | 67 |
| PEG 400 | 25° C. (RT) | 46 |
| Sorbitol Solution | 25° C. (RT) | 180 |
| Glycerol | 25° C. (RT) | 112 |
| 0.15% SLS | 25° C. (RT) | 50-58 |

Although the final concentrations may be larger than the currently authorized dosification of the solvents under study, the straightforward dissolving of methacetin, when heating the aqueous media at 55° C. for a short period of time, could not be possible to reproduce with the utilization of solvents as excipients. It is important to note that the solvents utilized were the most common ones in this type of preparations. Therefore, a gradient of temperature was utilized to completely dissolve the methacetin in the preparation. An in-process control testing was applied at this stage. A UV specific absorbance analytical method, without further manipulation of the sample, was utilized for confirming that the solid has been completely dissolved in the preparation.

It was surprisingly found that, when a solution of methacetin in purified water was prepared at 55° C. (Celsius), no p-anisidine appears. P-anisidine appeared only at a later stage when the methacetin solution was stored in a glass container. P-anisidine did not appear, even at a later stage, when the methacetin solution was stored in a plastic container.

Alternatively, longer dissolution at room temperature 20-25° C. were utilized. Table 6 summarizes the P-anisidine concentrations in methacetin solutions kept in PET, glass and glass type A containers for certain periods of time after dissolving methacetin at 25° C. P-anisidine appeared only at a later stage when the methacetin solution was stored in a glass container. P-anisidine did not appear at all even at a later stage when the methacetin solution was stored in a PET container.

A potential chemical mechanism involved in the decomposition of the product was hypotatized to be a type of Hofmann rearrangement of amides mechanism. The presence of hypochlorite type of anions, traces of which might be present in PW water, may develop a role in the decomposition of the $^{13}$C-methacetin. If this is the case, an alternative methodology and treatment (to prevent methacetin decomposition) of the aqueous media by hydrogen peroxide ($H_2O_2$), in order to convert the traces of hypoclorite ions into chloride species prior to the dissolution of the methacetin, may be utilized. In this context, the hypochlorite is reduced to chloride while the hydrogen peroxide is being oxidized to free oxygen.

A study to evaluate the effect of hydrogen peroxide on the stability of Methacetin was performed:

The experiment was performed using Methacetin API & 30% $H_2O_2$ to provide concentration of 0.00002% [30 microliter (μL) $H_2O_2$ in a 150 mL bottle].

The first step was to mix 30% $H_2O_2$ into boiled Purified water (PW), cooling to room temperature (RT) followed by dissolving Methacetin.

The solution was filled into glass bottles and placed under accelerated conditions (acc.) and RT conditions:

Stability results (up to 2 months) of Methacetin solutions under accelerated conditions is summarized in Table 7.

TABLE 6

P-anisidine concentrations in PET, glass and glass type A certain periods of time after dissolving methacetin at 25° C.

| Sample | | | | p-Anisidine (%); RRT = 0.86 | | | | | |
| --- | --- | --- | --- | --- | --- | --- | --- | --- | --- |
| Millstone | Batch No.: | Packaging | Medium | t = 0 | 1 Week Acc., | 2 Week Acc., | 1 Mo Acc., | 2 Mo Acc., | 3 Mo Acc., |
| A | RD-7195/1 | PET | Purified Water | ND* | ND* | ND* | ND* | ND* | ND* |
| A | RD-7195/2 | Glass | | ND* | ND* | ND* | ND* | 0.015 | 0.046 |
| A | RD-7195/3 | Glass Type A | | ND* | ND* | ND* | 0.04 | 0.04 | 0.073 |

(ND = not detected)

Therefore, according to some embodiments of the invention, it is determined that short term warming of the methacetin solution does not cause immediate degradation of the methacetin molecule. However, the degradation by-product (such as p-anisidine) appears at a later stage, as a secondary effect of the heating.

TABLE 7 p-Anisidine levels in methacetin solutions under accelerated stability conditions (40 Celsius degree).

| Sample | | | | p-Anisidine (%); RRT = 0.86 | | | | |
| --- | --- | --- | --- | --- | --- | --- | --- | --- |
| Millstone | Batch No.: | Packaging | Medium | t = 0 | 1 Week Acc., | 2 Week Acc., | 1 Mo Acc., | 2 Mo Acc., |
| C | Rb-7176/2 | Glass | Purified Water + $H_2O_2$ | ND* | 0.01 | NA | 0.01 | 0.96 |

(ND = not detected)

Up to 0.96% of p-Anisidine was detected in methacetin solution with added $H_2O_2$ under accelerated, stability conditions.

Based on the above data, $H_2O_2$ did not improve the stability of Methacetin solution.

Example C

Microbial Growth

Table 8 shows the microorganisms that were seeded in the methacetin compositions (formulation), according to embodiments of the invention, to check its properties. The media/target is the growing media utilized in the development of the colony.

TABLE 8

Microorganisms and media/targets

| Organism | ATCC Number | Media/Target |
|---|---|---|
| E. Coli | 8739 | TSA |
|  |  | Total Aerobic Count |
| S. aureus | 6538 | TSA |
|  |  | Total Aerobic Count |
| P. aeruginosa | 9027 | TSA |
|  |  | Total Aerobic Count |
| B. atrophaeus | 6633 | TSA |
|  |  | Total Aerobic Count |
| S. typhimurium | 14028 | TSA |
|  |  | Total Aerobic Count |
| C. albicans | 10231 | SDA + Chloram. |
|  |  | Total Yeasts and Molds |
| A. niger | 16404 | SDA + Chloram. |
|  |  | Total Yeasts and Molds |

Table 9 expresses a challenging test, in which the number of colonies observed in the control membrane and in the test membrane, where the methacetin compositions (formulation), according to embodiments of the invention, have been placed. The factor difference is obtained from the ratio between recovery on control membrane and recovery on test membrane. It is observed that the factor is about 1.

It was thus surprisingly found that the methacetin compositions (formulation), according to embodiments of the invention, do not inhibit the growth of microorganisms. If the factor was 1.4-1.5 or larger, which was not the case, this could mean that the methacetin compositions do inhibit the growth of microorganisms. No interaction between methacetin and bacteria is detected. The little amount of bacteria that may be present in the methacetin solution (under the threshold defined herein) do not affect the methacetin.

TABLE 9

Microorganism growth

| Microorgaism | Acutal Inoculum cfu | Recovery on Control Membrane cfu | Recovery on Test Membrane Cfu | Factor Difference |
|---|---|---|---|---|
| E. coli 8739 | 110 | 117 | 104 | 1.1 |
| S. aureus 6538 | 116 | 121 | 116 | 1.0 |
| P. aeruginosa 9027 | 106 | 111 | 101 | 1.1 |
| B. atrophaeus 6633 | 56 | 64 | 59 | 1.1 |
| S. typhimurium 14028 | 118 | 127 | 134 | 0.9 |
| C. albicans 10231 | 96 | 117 | 103 | 1.1 |
| A. niger 16404 | 35 | 34 | 34 | 1.0 |

Octanoate—for Evaluation of Insulin Resistance

Insulin resistance (IR) and nonalcoholic fatty liver disease (NAFLD), or its progression to the more severe liver disease—nonalcoholic steatohepatitis (NASH), are syndromes which co-exist in many patients and are most probably somehow interrelated; and there seems to be a link between IR and NAFLD and the metabolic syndrome.

While insulin resistance can be evaluated with relatively simple techniques like HOMA (Homeostatic model assessment) derived from:

$$\frac{\text{Glucose} \times \text{Insulin}}{405},$$

the gold standard for investigating and quantifying insulin resistance is the "hyperinsulinemic euglycemic clamp," so-called because it measures the amount of glucose necessary to compensate for an increased insulin level without causing of hypoglycemia. The clamp test is complicated, expensive and even risky, and additional tools are required to evaluate insulin resistance.

Insulin resistance can be peripheral and/or hepatic. Hepatic IR results in changes in glycogen synthesis and glycolysis An additional potential hepatic consequence is changes in synthesis and metabolization of fatty acids in the liver [Foufelle F, Ferre P. (2002) *New perspectives in the regulation of hepatic glycolytic and lipogenic genes by insulin and glucose: a role for the transcription factor sterol regulatory element binding protein*-1c. Biochem J 366:377-391, which is incorporated herein by reference in its entirety]

In addition, IR may cause a shift from carbohydrates metabolism towards fatty acids beta-oxidation [Randle P J, Garland P B, Hales C N, Newsholme E A. (1963) *The glucose fatty acid cycle: its role in insulin sensitivity and the metabolic disturbances in diabetes mellitus.* Lancet 1:785-789, which is incorporated herein by reference in its entirety].

Preliminary studies in 59 patients suffering from metabolic syndrome, demonstrated that octanoate highlight correlates with HOMA R>0.6, p<0.01.

Another preferred embodiment of the present invention is the use of the octanoate breath test as a tool to evaluate beta-oxidation in the context of insulin resistance.

Decreased sensitivity to insulin of cells, either in adipose tissue and skeletal muscles (peripheral), or in the liver, is defined as insulin resistance (IR).

IR may be associated with or cause metabolic pathways changes, some remain, normally or partially, sensitive to insulin, and are thus over activated by the high insulin levels (for example, fatty acid synthesis), while other pathways (for example, fatty acids oxidation or gluconeogenesis) might be instead over-activated or impaired.

Thus, insulin resistance might be detected by abnormal, increased, beta oxidation, which can be detected by yet another embodiment of the present invention by higher than normal metabolization of octanoic acid.

In yet another embodiment of the present invention, there is a method to evaluate changes in IR due to therapy by monitoring changes in octanoic acid metabolization.

What is claimed is:

1. A device for evaluating a liver condition of a subject, the device comprising:
one or more sensors adapted to sense an isotope level of a metabolic product of labeled methacetin or a salt or a derivative thereof in a breath of the subject; and
a processor adapted to receive data indicative of said isotope levels of said metabolic product of labeled methacetin and to compute a fluctuation parameter by estimation of the physiological noise in a percentage dose recovery (PDR) curve and/or a delta over baseline (DOB) curve of an isotope labeled methacetin or a salt or a derivative thereof, in comparison to a smooth curve, wherein a value of the fluctuation parameter being at or above a predetermined threshold is indicative of at least one liver condition of the subject, and wherein a value of the fluctuation parameter being below a predetermined threshold is indicative of a normal liver condition.

2. The device of claim 1, wherein isotope labeled methacetin, or a salt or a derivative thereof comprises carbon-13, carbon-14, oxygen-18 or any combination thereof.

3. The device of claim 1, wherein the liver condition comprises a liver related disease, malfunction, injury, transplantation, abnormality, fat accumulation, increased metabolism, decreased metabolism or a combination thereof.

4. The device of claim 1, wherein the processor is further adapted to follow-up of the at least one liver condition by re-computing, after a predetermined period of time, the fluctuation parameter from a liver breath test based on at least one of a percentage dose recovery (PDR) curve and a delta over baseline (DOB) curve of the isotope labeled methacetin, or a salt or a derivative thereof.

5. The device of claim 4, wherein the predetermined period of time comprises between 0.5 minutes and 4 hours.

6. The device of claim 4 wherein the predetermined period of time comprises between 4 hours and 12 months.

7. The device of claim 1, wherein said processor is further adapted to compute an output indication related to at least one liver condition of the subject, based at least on the fluctuation parameter.

8. A device of evaluating a liver condition of a subject, the device comprising:
one or more sensors adapted to sense an isotope level of a metabolic product of labeled methacetin or a salt or a derivative thereof in a breath of the subject; and
a processor adapted to receive data indicative of said isotope levels of said metabolic product of labeled methacetin and to compute a hepatic impairment score depending on a physiological noise in a percentage dose recovery (PDR) curve and/or a delta over baseline (DOB) curve of an isotope labeled methacetin, or a salt or a derivative thereof, in comparison to a smooth curve, and on a demographic parameter.

9. The device of claim 8, wherein the demographic parameter comprises, height, weight, age, gender, smoking habits, disease etiology, known information about complications, or any combination thereof.

10. The device of claim 8, wherein computing a hepatic impairment score is further depending on an appearance of an early peak.

11. The device of claim 8, wherein the contribution of one or more parameters to the hepatic impairment score depends on a value of the parameters.

12. The device of claim 8, wherein computing the hepatic impairment score comprises averaging the values of the parameters.

13. The device of claim 8, wherein computing the hepatic impairment score is performed based on the medical significance of the parameters.

14. The device of claim 8, wherein the hepatic impairment score is in the range of 1 to 10.

15. The device of claim 8, wherein an increase in hepatic impairment score is indicative of a deterioration in the liver condition of the subject.

16. The device of claim 8, wherein a decrease in hepatic impairment score is indicative of a improvement in the liver condition of the subject.

17. The device of claim 8, wherein the processor is further adapted to compute the trend of the hepatic impairment score.

18. The device of claim 8, wherein the hepatic impairment score is computed based on an expert decision system.

19. The device of claim 8, further comprising a display adapted to show the hepatic impairment score, the prediction of disease using a threshold for the hepatic impairment score, probability of disease, or any combinations thereof.

20. The device of claim 8, further comprising a display adapted to graphically show the hepatic impairment score, the trend of the hepatic impairment score, or both.

21. The device of claim 8, wherein the breath test related parameter comprises isotope ratio of a metabolic product of methacetin, or a salt or a derivative of methacetin, in the subject's breath.

22. A device for evaluating a liver condition of a subject, the device comprising:
one or more sensors adapted to sense an isotope level of a metabolic product of labeled methacetin or a salt or a derivative thereof in a breath of the subject; and
a processor receiving data indicative of said isotope levels of said metabolic product of labeled methacetin and evaluating hepatic venous pressure gradient (HVPG) and/or number of shunts as detected by a physiological noise in a percentage dose recovery (PDR) curve and/or a delta over baseline (DOB) curve of an isotope labeled methacetin, or a salt or a derivative thereof, in comparison to a smooth curve.

23. The device of claim 22, wherein said isotope labeled methacetin, or a salt or a derivative thereof comprises carbon-13, carbon-14, oxygen-18 or any combination thereof.

24. The device of claim 22, wherein the liver condition comprises a liver related disease, malfunction, injury, transplantation, abnormality, fat accumulation, increased metabolism, decreased metabolism or a combination thereof.

25. The device of claim 22, wherein the processor is further adapted to follow-up the liver condition by re-evaluating, after a predetermined period of time, the hepatic venous pressure gradient (HVPG) and/or the number of shunts based the isotope labeled methacetin breath test.

26. The device of claim 25, wherein the predetermined period of time comprises between 0.5 minutes and 4 hours.

27. The device of claim 25 wherein the predetermined period of time comprises between 4 hours and 12 months.

28. The device of claim 22, wherein said processor is further adapted to compute an output indication related to the liver condition of the subject, based at least on the evaluation of the hepatic venous pressure gradient (HVPG) and/or the number of shunts.

* * * * *